United States Patent
Stihl

(10) Patent No.: US 7,081,119 B2
(45) Date of Patent: Jul. 25, 2006

(54) DRILL GUIDE ASSEMBLY FOR A BONE FIXATION DEVICE

(75) Inventor: Pascal Stihl, West Chester, PA (US)

(73) Assignee: HFSC Company, West Chester, PA (US)

( * ) Notice: Subject to any disclaimer, the term of this patent is extended or adjusted under 35 U.S.C. 154(b) by 0 days.

(21) Appl. No.: 10/903,649

(22) Filed: Jul. 30, 2004

(65) Prior Publication Data

US 2005/0027301 A1 Feb. 3, 2005

Related U.S. Application Data

(60) Provisional application No. 60/491,898, filed on Aug. 1, 2003.

(51) Int. Cl.
*A61B 17/58* (2006.01)
*A61F 2/00* (2006.01)

(52) U.S. Cl. .................................................. 606/96
(58) Field of Classification Search ............... 60/53, 60/60, 69, 70, 71, 72, 73, 86, 96, 97, 98
See application file for complete search history.

(56) References Cited

U.S. PATENT DOCUMENTS

| | | | |
|---|---|---|---|
| 1,831,813 A | 11/1931 | Levedahl |
| 2,181,746 A | 11/1939 | Siebrandt |
| 2,200,120 A | 5/1940 | Nauth |
| 2,424,485 A | 7/1947 | Miller |
| 2,494,229 A | 1/1950 | Collison |
| 2,607,339 A | 8/1952 | Price |
| 2,670,637 A | 2/1954 | Edmunds |
| 2,674,906 A | 4/1954 | Timpner |
| 3,071,030 A | 1/1963 | Larry |
| 3,540,322 A | 11/1970 | Swanson |
| 3,727,611 A | 4/1973 | Schultz |
| 4,119,092 A | 10/1978 | Gil |
| 4,388,921 A | 6/1983 | Sutter et al. |
| 4,450,835 A | 5/1984 | Asnis et al. |
| 4,493,317 A | 1/1985 | Klaue |
| 4,646,413 A | 3/1987 | Nall et al. |
| 4,668,134 A | 5/1987 | Vindez |
| D291,246 S | 8/1987 | Lower |
| 4,744,353 A | 5/1988 | McFarland |
| 4,787,377 A | 11/1988 | Laboureau |
| 4,788,970 A | 12/1988 | Karas et al. |
| 4,791,918 A | 12/1988 | Von Hasselbach |
| 4,803,976 A | 2/1989 | Frigg et al. |
| 4,872,451 A | 10/1989 | Moore et al. |

(Continued)

FOREIGN PATENT DOCUMENTS

CH 655646 A5 5/1986

(Continued)

*Primary Examiner*—Eduardo C. Robert
*Assistant Examiner*—Anuradha Ramana
(74) *Attorney, Agent, or Firm*—Jones Day

(57) ABSTRACT

A drill guide has a handle for holding and is configured to actuate a plate-engaging mechanism. An elongated member extends between proximal and distal portions with the proximal portion associated with the handle portion and the distal portion associated with the plate-engaging mechanism. The plate-engaging mechanism is actuated by an actuating member actuated by the second handle portion. The drill guide includes at least one guide sleeve rotatably coupled to the elongated member by a proximal and distal coupler. Furthermore, the plate-engaging mechanism includes a bone plate-engaging portion configured to couple with a bone plate when the second handle portion is moved in a first direction with respect to said first handle portion.

58 Claims, 22 Drawing Sheets

U.S. PATENT DOCUMENTS

| | | |
|---|---|---|
| 4,898,502 A | 2/1990 | Becher |
| 4,911,153 A | 3/1990 | Border |
| 4,941,781 A | 7/1990 | Becher |
| 4,969,781 A | 11/1990 | Fahrner et al. |
| 5,026,376 A | 6/1991 | Greenberg |
| 5,030,219 A | 7/1991 | Matsen, III et al. |
| 5,054,968 A | 10/1991 | Eckman |
| 5,071,293 A | 12/1991 | Wells |
| 5,112,336 A | 5/1992 | Krevolin et al. |
| 5,133,720 A | 7/1992 | Greenberg |
| 5,147,367 A | 9/1992 | Ellis |
| 5,154,720 A | 10/1992 | Trott et al. |
| 5,207,753 A | 5/1993 | Badrinath |
| 5,250,055 A | 10/1993 | Moore et al. |
| 5,281,056 A | 1/1994 | Lawson et al. |
| 5,306,278 A | 4/1994 | Dahl et al. |
| 5,312,412 A | 5/1994 | Whipple |
| 5,324,295 A | 6/1994 | Shapiro |
| 5,364,399 A | 11/1994 | Lowery et al. |
| D357,534 S | 4/1995 | Hayes |
| 5,409,493 A | 4/1995 | Greenberg |
| D359,557 S | 6/1995 | Hayes |
| 5,423,826 A | 6/1995 | Coates et al. |
| 5,429,641 A | 7/1995 | Gotfried |
| 5,437,677 A | 8/1995 | Shearer et al. |
| 5,458,602 A | 10/1995 | Goble et al. |
| 5,484,446 A | 1/1996 | Burke et al. |
| 5,507,801 A | 4/1996 | Gisin et al. |
| 5,575,794 A | 11/1996 | Walus et al. |
| 5,584,839 A | 12/1996 | Gieringer |
| 5,595,193 A | 1/1997 | Walus et al. |
| 5,601,550 A | 2/1997 | Esser |
| 5,601,553 A | 2/1997 | Trebing et al. |
| 5,624,447 A | 4/1997 | Myers |
| 5,634,927 A | 6/1997 | Houston et al. |
| 5,637,112 A | 6/1997 | Moore et al. |
| D382,056 S | 8/1997 | Kammerer |
| 5,669,915 A | 9/1997 | Caspar et al. |
| 5,676,666 A | 10/1997 | Oxland et al. |
| 5,700,267 A | 12/1997 | Urbanski |
| 5,722,978 A | 3/1998 | Jenkins, Jr. |
| 5,725,532 A | 3/1998 | Shoemaker |
| 5,741,266 A | 4/1998 | Moran et al. |
| 5,743,916 A | 4/1998 | Greenberg et al. |
| 5,746,743 A | 5/1998 | Greenberg |
| 5,746,763 A | 5/1998 | Benderev et al. |
| 5,749,884 A | 5/1998 | Benderev et al. |
| 5,755,721 A | 5/1998 | Hearn |
| 5,766,221 A | 6/1998 | Benderev et al. |
| 5,769,856 A | 6/1998 | Dong et al. |
| D397,220 S | 8/1998 | Kumar et al. |
| D398,996 S | 9/1998 | Simmons et al. |
| 5,836,950 A | 11/1998 | Hansson |
| RE36,020 E | 12/1998 | Moore et al. |
| 5,851,207 A | 12/1998 | Cesarone |
| D404,126 S | 1/1999 | Asfora |
| 5,888,034 A | 3/1999 | Greenberg |
| 5,895,390 A | 4/1999 | Moran et al. |
| 5,910,143 A | 6/1999 | Cripe et al. |
| 5,913,860 A | 6/1999 | Scholl |
| 5,938,686 A | 8/1999 | Benderev et al. |
| 5,947,654 A | 9/1999 | Blankenship et al. |
| 5,951,561 A | 9/1999 | Pepper et al. |
| 5,954,722 A | 9/1999 | Bono |
| 5,957,927 A | 9/1999 | Magee et al. |
| 5,961,257 A | 10/1999 | Bettini et al. |
| 5,961,530 A | 10/1999 | Moore et al. |
| 6,007,535 A | 12/1999 | Rayhack et al. |
| 6,013,083 A | 1/2000 | Bennett |
| 6,019,767 A | 2/2000 | Howell |
| 6,036,696 A | 3/2000 | Lambrecht et al. |
| 6,059,789 A | 5/2000 | Dinger et al. |
| 6,066,142 A | 5/2000 | Serbousek et al. |
| 6,113,637 A | 9/2000 | Gill et al. |
| 6,139,550 A | 10/2000 | Michelson |
| D433,506 S | 11/2000 | Asfora |
| 6,143,012 A | 11/2000 | Gausepohl |
| 6,152,927 A | 11/2000 | Farris et al. |
| 6,193,721 B1 | 2/2001 | Michelson |
| 6,193,723 B1 | 2/2001 | Cripe et al. |
| 6,206,886 B1 | 3/2001 | Bennett |
| 6,210,415 B1 | 4/2001 | Bester |
| 6,235,034 B1 | 5/2001 | Bray |
| 6,238,400 B1 | 5/2001 | Bays |
| 6,241,729 B1 | 6/2001 | Estes et al. |
| 6,258,091 B1 | 7/2001 | Sevrain et al. |
| 6,283,969 B1 | 9/2001 | Grusin et al. |
| 6,287,313 B1 | 9/2001 | Sasso |
| 6,299,616 B1 | 10/2001 | Beger |
| 6,306,139 B1 | 10/2001 | Fuentes |
| 6,330,845 B1 | 12/2001 | Meulink |
| 6,342,056 B1 | 1/2002 | Mac-Thiong et al. |
| 6,342,057 B1 | 1/2002 | Brace et al. |
| 6,361,537 B1 | 3/2002 | Anderson |
| 6,371,959 B1 | 4/2002 | Trice |
| 6,379,364 B1 | 4/2002 | Brace et al. |
| 6,383,186 B1 | 5/2002 | Michelson |
| 6,398,783 B1 | 6/2002 | Michelson |
| 6,416,518 B1 | 7/2002 | DeMayo |
| 6,416,528 B1 | 7/2002 | Michelson |
| 6,419,678 B1 | 7/2002 | Asfora |
| 6,428,542 B1 | 8/2002 | Michelson |
| 6,436,103 B1 | 8/2002 | Suddaby |
| 6,447,512 B1 | 9/2002 | Landry et al. |
| 6,454,771 B1 | 9/2002 | Michelson |
| 6,475,190 B1 | 11/2002 | Young |
| 6,491,714 B1 | 12/2002 | Bennett |
| 6,524,238 B1 | 2/2003 | Velikaris et al. |
| 6,524,312 B1 | 2/2003 | Landry et al. |
| 6,527,776 B1 | 3/2003 | Michelson |
| 6,533,786 B1 | 3/2003 | Needham et al. |
| 6,558,089 B1 | 5/2003 | DeBlasio |
| 6,562,046 B1 | 5/2003 | Sasso |
| 6,565,571 B1 | 5/2003 | Jackowski et al. |
| RE38,684 E * | 1/2005 | Cesarone .................... 606/69 |
| 2001/0027320 A1 | 10/2001 | Sasso |
| 2001/0047172 A1 | 11/2001 | Foley et al. |
| 2002/0004661 A1 | 1/2002 | Sevrain et al. |
| 2002/0022847 A1 | 2/2002 | Ray, III et al. |
| 2002/0045896 A1 | 4/2002 | Michelson |
| 2002/0082606 A1 | 6/2002 | Suddaby |
| 2002/0120273 A1 | 8/2002 | Needham et al. |
| 2002/0128655 A1 | 9/2002 | Michelson |
| 2002/0133172 A1 | 9/2002 | Lambrecht et al. |
| 2002/0147450 A1 | 10/2002 | LeHuec et al. |
| 2002/0183754 A1 | 12/2002 | Michelson |
| 2003/0018335 A1 | 1/2003 | Michelson |
| 2003/0040748 A1 | 2/2003 | Aikins et al. |
| 2003/0040752 A1 | 2/2003 | Kitchens |
| 2003/0040753 A1 | 2/2003 | Daum et al. |
| 2003/0045880 A1 | 3/2003 | Michelson |
| 2003/0055430 A1 | 3/2003 | Kim |
| 2003/0083661 A1 | 5/2003 | Orbay et al. |
| 2003/0083667 A1 | 5/2003 | Ralph et al. |

FOREIGN PATENT DOCUMENTS

| | | |
|---|---|---|
| DE | 3222037 A1 | 4/1984 |
| DE | 4238582 A1 | 5/1994 |
| EP | 281763 A2 | 9/1988 |
| EP | 495488 A2 | 1/1991 |
| EP | 506213 A1 | 2/1991 |
| EP | 518071 A1 | 12/1992 |
| EP | 591985 A1 | 4/1994 |

| | | | | | | |
|---|---|---|---|---|---|---|
| EP | 518071 | B1 | 10/1994 | WO | WO 93/19678 A2 | 10/1993 |
| EP | 281763 | B1 | 12/1998 | WO | WO 95/11632 A1 | 5/1995 |
| EP | 962190 | A2 | 12/1999 | WO | WO 96/05778 A1 | 2/1996 |
| EP | 995403 | A1 | 4/2000 | WO | WO 96/15727 A1 | 5/1996 |
| EP | 1132052 | A2 | 9/2001 | WO | WO 96/20650 A1 | 7/1996 |
| FR | 2713473 | A1 | 6/1995 | WO | WO 98/34553 A1 | 8/1998 |
| FR | 2735008 | A1 | 12/1996 | WO | WO 99/21502 A1 | 5/1999 |
| FR | 2784570 | A1 | 4/2000 | WO | WO 99/52453 A2 | 10/1999 |
| GB | 2243316 | A | 10/1991 | WO | WO 01/01874 A1 | 1/2001 |
| GB | 2324967 | A | 11/1998 | WO | WO 02/02999 A1 | 1/2002 |
| JP | 2236331 | A | 9/1990 | WO | WO 02/080791 A1 | 10/2002 |
| JP | 5031116 | A | 2/1993 | WO | WO 03/007826 A1 | 1/2003 |
| JP | 10-328205 | A | 12/1998 | | | |
| JP | 2001-245894 | A | 9/2001 | | | |

\* cited by examiner

DRILL GUIDE ASSEMBLY FOR A BONE FIXATION DEVICE

CROSS-REFERENCE TO RELATED APPLICATIONS

The present application claims priority under 35 U.S.C. § 119(e) to U.S. Provisional Application Ser. No. 60/491,898, filed Aug. 1, 2003, the disclosure of which is incorporated by reference herein in its entirety.

FIELD OF THE INVENTION

The present invention relates to a drill guide, such as for example, a surgical drill guide that is removably attachable to a fixation device, such as for example, a bone plate. More particularly, the surgical drill guide assembly provides soft tissue protection and precise alignment of at least one drill tube with bone screw holes of a bone plate, such as for example, a spinal bone plate.

BACKGROUND OF THE INVENTION

The use of surgical fixation plates for a variety of orthopedic applications is widely accepted. The plates are used by surgeons to stabilize, mend, or align a patient's bone as well as alter compression of patient's bones, and are typically fastened to the bones with a plurality of fasteners, such as, screws that are installed through holes in the plate. Proper orientation and alignment of fasteners and secure surgical fixation of the plate can mitigate some of the potential complications after implantation.

Locking bone plates used in spinal applications must be installed with special care, as the plates may be used for long term, intravertebral fixation, bone-fragment fixation, and anterior decompression of vertebra of the spine. The margin for error in spinal surgery is small, particularly because of the sensitivity of the spinal cord and the risk inherent with invasive procedures around the spinal cord. Furthermore, the dimensions of vertebral bone available for setting fasteners are fairly constrained.

Screws, used to secure the plate to the bone, should be properly aligned with the associated fixation plate hole so that each screw is seated correctly within the plate. Any misalignment of the screw within the plate hole risks tissue damage. In addition, improperly seated screws may result in an unstable or insecure connection of the plate to the bony material, thus potentially defeating the usefulness of the plate. Locking plates, in particular, demand precise fastener alignment.

Drill guides are often used to assist the surgeon in aligning the screws with the plate holes. Drill guides for locking plates attach or abut to the plate and generally include a guide tube for guiding a drill bit. One drawback of traditional drill guides is that the drill guides do not provide adequate soft tissue protection. This is of particular concern when the surgeon is installing the plate using an anterior approach to the spine through the abdomen or chest region. Many sensitive and vital organs reside in the chest and abdomen and a surgeon must be especially careful not to damage these organs when operating on the spine. Thus, the surgeon must proceed with caution, requiring more time for the procedure and thus increasing the chance of complications for the patient under anesthesia.

Another drawback of conventional drill guides is that they do not engage the plate in a manner that prevents lateral or rotational movement of the plate with respect to the drill guide.

SUMMARY OF THE INVENTION

According to one embodiment, there is provided a system and method for quickly and securely attaching a drill guide to a bone plate that resists rotational movement, requires minimal space within a surgical workspace, and provides tissue protection through an anterior spinal approach.

In one embodiment a surgical drill guide assembly includes a handle that is to be held by a user and configured to actuate a plate-engaging mechanism. The handle is assembled from first and second handle portions that are movably connected to each other. The drill guide also includes an elongated member having proximal and distal portions and a length. The proximal portion of the elongated member is associated with the first handle portion and the distal portion of the elongated member is associated with the plate-engaging mechanism. An actuating member, having proximal and distal portions and a length therebetween, engages the second handle portion at the elongated member proximal portion and the plate-engaging mechanism at the member distal end. Furthermore, at least one guide sleeve is included on the drill guide and has a proximal and a distal portion and a length therebetween. The proximal portions of the guide sleeve and the elongated member are coupled to each other by a proximal coupling member and the distal portions of the guide sleeve and the elongated member are coupled together by a distal coupling member. The proximal and distal coupling members are not of the same length, which may allow the longitudinal axis of the guide barrel to be configured at a non-zero angle with respect to the longitudinal axis of the elongated member. Additionally, the length of the guide sleeve is substantially the same as the length of the elongated member, and the plate-engaging mechanism further comprises a bone plate-engaging portion configured to couple with a bone plate when the second handle portion is moved in a first direction with respect to said first handle portion.

According to another embodiment, the surgical drill guide first and second handle portions are pivotally connected. The handle further comprising a spring, the handle further having an actuated state and a non-actuated state wherein the spring associated with at least the first or second handle portion to bias the handle to the non-actuated state.

In yet another embodiment, the surgical drill guide includes a plate-engaging member and a locking assembly, wherein when the plate-engaging member contacts a correspondingly configured recess in a bone plate, the locking assembly is operable to lock the plate-engaging mechanism to the plate without further operation by the user. Furthermore, the locking assembly includes a sliding latch having a detent. The proximal portion of the elongated member is fixed to the first handle portion and the distal end of the elongated member is fixed to the plate engaging mechanism.

According to still another embodiment, the elongated member is integral with the first handle portion and the actuating member is integral with the second handle portion. Additionally, the plate-engaging mechanism can engage a hole in the plate which aligns the at least one guide sleeve with a different hole in the plate.

In another embodiment, the elongated member is fixed to the proximal and distal coupling members. The actuating member slidably engages the plate-engaging mechanism, and the actuating member further comprises an actuating pin at the distal end for engaging the plate-engaging mechanism.

In a further embodiment, the actuating pin is tapered at one end to correspond with a tapered bore in the plate-engaging mechanism. Additionally, the plate-engaging mechanism further comprises a locator pin for engaging a slot in the bone plate, the locator pin operable to rotatably fix the drill guide to the bone plate. Furthermore, the locator pin is disposed substantially parallel with a longitudinal axis of the drill guide, and the plate-engaging mechanism further comprises at least one resilient finger sized and configured to be radially expanded for engagement within a slot within the bone plate.

In a further embodiment, when the drill guide engages the bone plate and the bone plate engages a spinal bone during an anterior approach surgical procedure on the thoracic, lumbar or sacral spine, at least a portion of the guide sleeve is located outside of the patient's body. The length of the guide sleeve is from about 50 millimeters (mm) to about 400 mm, and the length of the guide sleeve is about 250 mm to about 270 mm. Furthermore, the guide sleeve is sized to slidably accept at least one surgical tool for performing a surgical procedure, and the guide sleeve inner diameter is from about 4 mm to about 15 mm, wherein alternatively the guide sleeve inner diameter is about 8.0 mm to about 8.5 mm.

According to yet another embodiment, the guide sleeve proximal portion further comprises a flange having stop surface, the stop surface configured to contact a corresponding stop surface on a surgical tool when the tool is moved in a first direction within the guide tube, wherein when the corresponding surfaces contact each other the stop surfaces prevent the tool surface from further movement in the first direction. Additionally, the guide sleeve has a longitudinal axis inclined from about 0 degrees to about 8 degrees with respect to a longitudinal axis of the elongated member, and wherein the guide sleeve has also may have a longitudinal axis inclined about 2.0 to about 2.5 degrees with respect to the longitudinal axis of the elongated member.

In another embodiment, at least a first and second guide sleeves is included for accepting at least one tool for use in a surgical procedure, and the first guide sleeve has a first longitudinal axis and the second guide sleeve has a second longitudinal axis, and wherein the first and second guide sleeves are disposed on opposite sides of the elongated member. Furthermore, the drill guide is configured for use as a plate holder.

According to another embodiment, the first and second handle portions are pivotally connected, and the handle further comprising a spring, the handle further having an actuated state and a non-actuated state, said spring associated with at least the first or second handle portion to bias the handle in the non-actuated state. Additionally, the plate engaging mechanism further comprising a plate-engaging member and a locking assembly, wherein when the plate-engaging member contacts a correspondingly configured recess in a bone plate, the locking assembly is operable to lock the plate-engaging mechanism to the plate without further operation by the user. Furthermore, the locking assembly includes a sliding latch having a detent.

In yet another embodiment, the proximal portion of the elongated member is fixed to the first handle portion and the distal end of the elongated member is fixed to the plate engaging mechanism. In addition, the elongated member is fixed to the proximal and distal coupling members. The actuating member slidably engages the plate-engaging mechanism, and the actuating member further comprises an actuating pin at the member distal end for engaging the plate-engaging mechanism. Furthermore, the actuating pin is tapered at one end to correspond with a tapered bore in the plate-engaging mechanism and the plate-engaging mecha-nism further comprises a locator pin for engaging a slot in the bone plate, the locator pin operable to rotatably fix the drill guide to the bone plate.

According to still another embodiment, the locator pin is disposed substantially parallel with a longitudinal axis of the drill guide, and the plate-engaging mechanism further comprises at least one resilient finger sized and configured to be radially expanded for engagement within a slot within the bone plate. Additionally, when the drill guide engages the bone plate and the bone plate engages a spinal bone during an anterior approach surgical procedure on the thoracic, lumbar or sacral spine, at least a portion of the guide sleeve is located outside of the patient's body. The length of the guide sleeve is from about 50 millimeters (mm) to about 400 mm, and may be about 250 mm to about 270 mm.

In still another embodiment, the guide sleeve is sized to slidably accept at least one surgical tool for performing a surgical procedure. The guide sleeve inner diameter is from about 4 mm to about 15 mm, and about 8.0 mm to about 8.5 mm. In addition, the guide sleeve proximal portion further comprises a flange having stop surface, the stop surface configured to contact a corresponding stop surface on a surgical tool when the tool is moved in a first direction within the guide tube, wherein when the corresponding surfaces contact each other the stop surfaces prevent the tool surface from further movement in the first direction.

Still according to another embodiment, the guide sleeve has a longitudinal axis inclined from about 0 degrees to about 8 degrees with respect to a longitudinal axis of the elongated member, or is inclined about 2.0 to about 2.5 degrees with respect to the longitudinal axis of the elongated member. Still further, at least first and second guide sleeves are provided for accepting at least one tool for use in a surgical procedure. Further, the first guide sleeve has a first longitudinal axis and the second guide sleeve has a second longitudinal axis, and wherein the first and second guide sleeves are disposed on opposite sides of the elongated member. In addition, the drill guide is configured for use as a plate holder, and the pivot members comprise elongated member-engaging portions for engaging the elongated member and guide sleeve-engaging portions for engaging the guide sleeve.

In yet a further embodiment, the first pivot member is coupled to the elongate member with a pin and the second pivot member is coupled with the plate-engaging mechanism with a pin. The first position is a left position and said second position is a right position with respect to said elongated member, and the pivot members are configured to rotate about 180 degrees. Furthermore, the pivot members are configured to align the guide sleeve with a left screw bore of the plate when in the left most position and a right screw bore of the plate when in the right most position. In addition, an angle between a central axis of the guide sleeve with respect to a longitudinal axis of the elongated member is maintained whether the guide sleeve is in a left or right position.

According to another embodiment of the present invention, a method for using a drill guide for anterior spinal plating includes gripping a handle of a drill guide comprising an elongated portion, plate-engagement portion, and guide sleeve. Further included is the steps of positioning a plate engagement mechanism within a slot of a bone plate and squeezing the handle to actuate an actuation arm and thereby the plate engagement mechanism such that the plate engagement mechanism firmly engages an inner surface of the slot of the bone plate. Steps further include, translating a latch to engage a ball detent such that the actuation arm is refrained from returning to a non-actuated state and inserting the drill guide and engaged bone plate anteriorly through an incision toward a surgical site on the vertebral column wherein an end of the guide sleeve nearest the operators is maintained anterior to the incision.

According to another embodiment, the method further includes the steps of positioning a locating member within the slot of the bone plate, wherein the surgical site on the vertebral column is the thoracic vertebra. Additionally, the surgical site on the vertebral column is the lumbar vertebra and/or the surgical site on the vertebral column is from about T1 to about S1 vertebrae.

In an alternative embodiment, a method for using a drill guide for anterior spinal plating includes the steps of gripping a handle of a drill guide and positioning a plate engagement mechanism within a slot of a bone plate. Next, a surgeon squeezes the handle, thereby actuating an actuation arm and thus the plate engagement mechanism such that the plate engagement mechanism firmly engages an inner surface of the slot of the bone plate. The surgeon then translates a latch located on the handle which engages a ball detent such that the actuation arm is refrained from returning to a non-actuated state. The surgeon then inserts the drill guide and engaged bone plate anteriorly through an incision toward a surgical site on the vertebral column. Thereafter, surgical tools are then inserted into the guide sleeve and surgical procedures are executed through the distal end of the guide sleeve.

According to still another embodiment, the surgeon then locks the plate-engaging mechanism so that the drill guide remains attached to the bone plate. Next, the surgeon inserts a drill bit down the guide sleeve and drills a hole in the vertebrae. Following drilling of the hole, the surgeon places a bone fastener down the guide sleeve and inserts the bone fastener through an aperture in the bone plate and into a vertebrae. Finally, the surgeon releases the drill guide assembly from the bone plate.

In still another embodiment, a method of attaching a spinal bone fixation device to the spine includes providing access to the anterior region of the spine to receive the bone plate where the bone plate has a plurality of holes. Next, the method provides a guide assembly comprising a plate engaging mechanism for attaching the guide assembly to the plate, a handle to actuate the plate engaging mechanism and a guide sleeve to guide either an instrument or a bone fastener or both at an appropriate angle through a bone fastener hole in a bone fixation device. The method next places the bone plate in contact with the spine and attaches the guide assembly to at least one of the holes in the bone plate such that the distal portion of the guide sleeve is adjacent or contacting the bone plate and the proximal portion of the guide sleeve extends anteriorly beyond the surgical incision in the patient. Furthermore, a bone fastener is provided down the guide sleeve and a surgeon attaches the bone fastener through a hole in the plate into a vertebrae.

According to yet another embodiment, the method further includes inserting a drill bit down the guide sleeve and drilling a hole in a vertebrae. Also provided is a guide assembly for guiding either an instrument or bone fastener at an appropriate angle with respect to a bone fixation device. The guide assembly includes a bone fixation device engaging mechanism having at least one radially extending member that engages at least one of the plurality of holes in the bone fixation device. The guide assembly also includes a handle to be held by a user and configured to activate the engaging mechanism to attach the guide assembly to the bone fixation device, the handle has first and second handle portions moveable with respect to each other to attach and release the guide assembly to the bone fixation device. Further included is an elongated member having proximal and distal portions and a longitudinal axis, the proximal portion associated with the first handle portion and the distal portion associated with the engaging mechanism. An actuating member is also included that has proximal and distal portions, the proximal portion associated with the second handle position and the distal portion associated with the engaging mechanism. At least one guide sleeve is provided and has proximal and distal portions and a longitudinal axis, the guide sleeve sized to receive and guide either an instrument or bone fastener or both. Further included is a proximal coupling member coupling the proximal portion of the guide sleeve to the elongated member and a distal coupling member coupling the distal portion of the guide sleeve to the elongated member. The longitudinal axis of the elongated member is angled with respect to the longitudinal axis of the guide sleeve and the distal portion of the guide sleeve is aligned with a different hole than the hole engaged by the plate engaging mechanism. In yet another embodiment, the guide sleeve is configured and adapted to protect soft tissue during the medical procedure.

BRIEF DESCRIPTION OF THE DRAWINGS

For a better understanding of the nature and objects of the invention, reference should be made to the following detailed description, taken in conjunction with the accompanying drawings which show preferred features of the invention, in which like reference numerals refer to corresponding parts throughout the several views of the drawings and wherein:

FIGS. 3–5A show a handle assembly of the drill guide of FIG. 1;

DETAILED DESCRIPTION OF THE INVENTION

Figure 1:
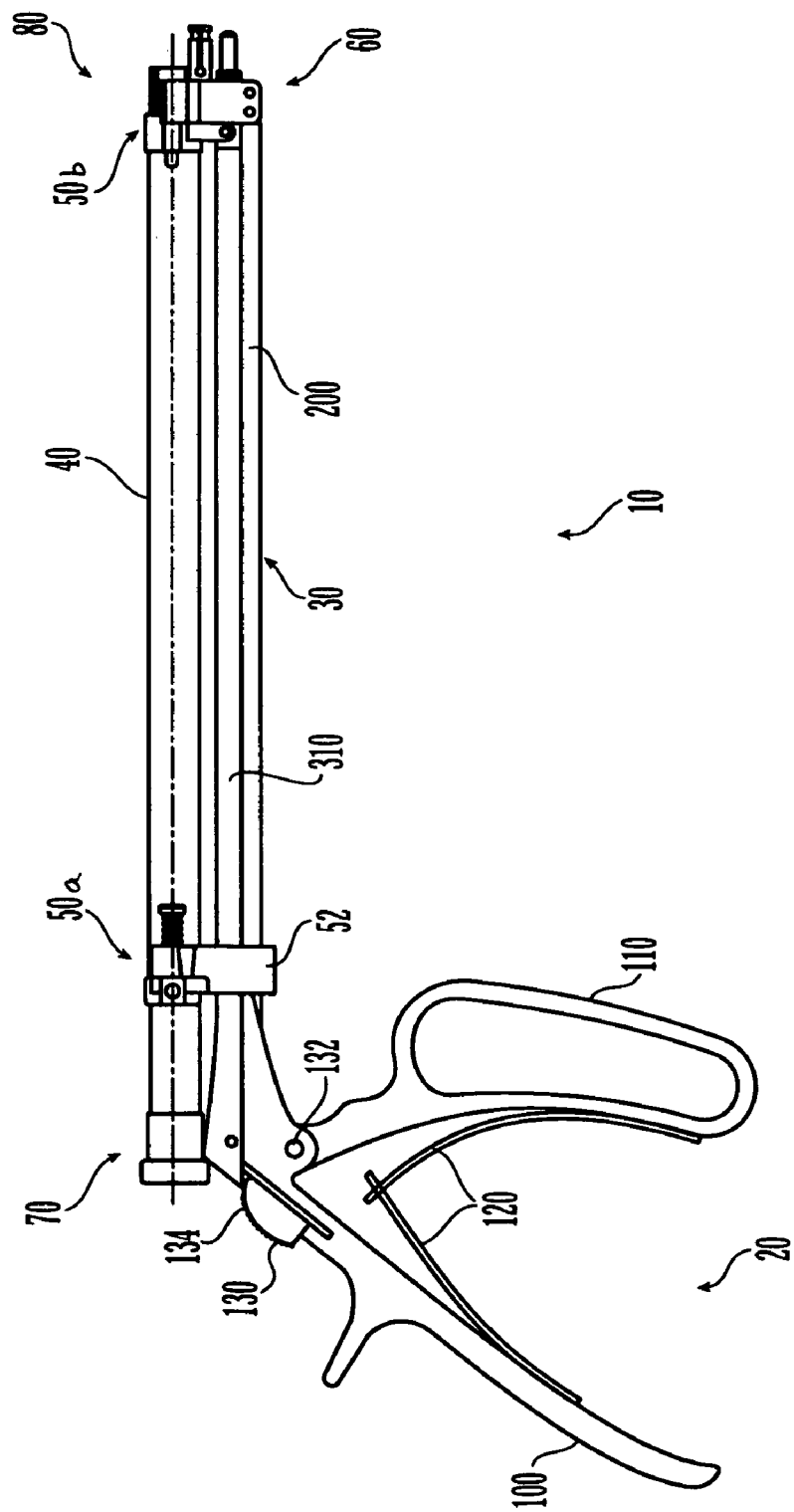
FIG. 1 shows a side view of a drill guide according to one embodiment of the present invention.

Referring to FIG. 1, there is shown an exemplary drill guide assembly 10, which is adapted for use with a spine fixation device, such as for example, a bone plate 500. While the drill guide assembly is disclosed in conjunction with a spinal plate it is contemplated that the drill guide assembly may be used in conjunction with bone plates used on any portion of the body. Drill guide assembly 10 generally includes an actuating handle 20, a body assembly 30, a guide barrel or barrels 40, a plate engaging and aligning mechanism 60, and optionally for the single barrel variety assembly, pivoting mechanisms 50a. 50b. In general, to operate the drill guide assembly 10, a surgeon grasps the actuating handle 20 of the drill guide assembly 10. The surgeon then aligns the plate engaging and aligning mechanism 60 with a bone plate such that plate attachment mechanism 850 (FIG. 14) and locator pin 814 (FIG. 14) engage a slot 520, 510 (FIG. 19), respectively, in the bone plate. Once the plate attachment mechanism 850 and locator pin 814 are aligned with the slot 520, 510 in the plate the surgeon squeezes actuation handle 20. Squeezing actuation handle 20 moves an actuation bar 310 toward the plate engaging end of the drill guide assembly 10, thereby pushing taper pin 900 (FIG. 17) through a taper pin bore 854 (FIG. 15) in the plate attachment mechanism 850. The plate attachment mechanism has a plurality of expandable fingers 852 disposed about the taper pin bore, and as the taper pin 900 moves it engages the inner walls of the taper pin bore 854 and causes the fingers 852 to radially expand and engage slot 520 in the bone plate, thus locking the drill guide to the plate. The drill guide 10 and bone plate may be coupled together in this manner before the plate is inserted into the incision, thereby allowing the surgeon to use the drill guide as a plate holder. The plate may then be inserted into the incision and placed at the targeted bone site using the drill guide 10, thus eliminating the need for a separate plate holding and placing tool to place and hold the bone plate in place within the surgical site. Subsequently, the drill guide may be disconnected from the plate by releasing the handles, whereupon the expandable fingers return to their unexpanded state, moving the taper pin and actuating bar rearward, toward the handle.

As shown in FIG. 1, actuating handle 20 generally includes a stationary grip 100 and a pivot grip 110 biased away from stationary grip 100 by a leaf spring 120 that biases the two grips away from each other. In use, a surgeon aligns the assembly 10 with a bone plate (described below) and squeezes pivot grip 110 toward stationary grip 100. This motion is translated to the plate engaging and aligning mechanism 60 which locks assembly 10 to the bone plate. The surgeon can then slide latch 130 linearly along an axis parallel to stationary handle 100, thereby locking actuating handle 20 in an actuated position and locking assembly 10 to the plate, thus allowing the surgeon to release his/her hand from actuating handle 20.

Figure 3:
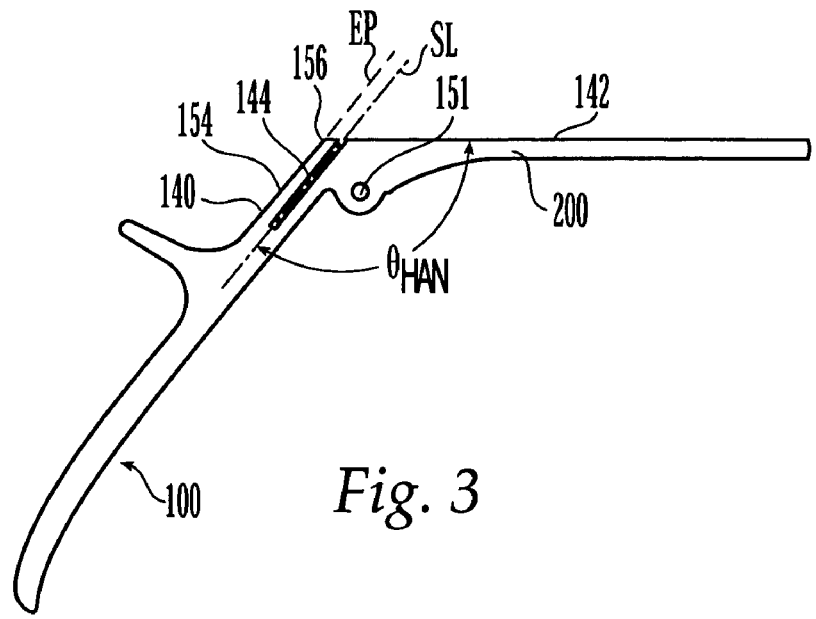
Figure 4:
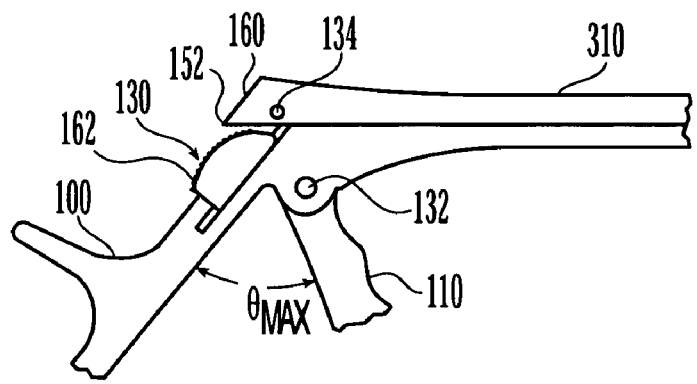

FIGS. 3–5 show actuating handle 20 in greater detail. Pivot grip 110 is pivotably attached to a proximal end of body assembly 30 by an actuation pin 132. Throughout this specification, unless otherwise noted, the use of the term 'proximal' will refer to the end of the device that is nearest the user and the term 'distal' will refer to the end of the device that is nearest the surgical site during use. Leaf springs 120 (FIG. 1) are fastened to stationary grip 100 and pivot grip 110 to bias actuating handle 20 in a non-actuated position.

As shown in FIG. 3, stationary grip 100 has two generally straight sections, grip section 140 and body section 142. Grip section 140 has an upper slotted portion 144 that is disposed along line SL. Upper slotted portion 144 does not extend all the way through stationary grip 100. Instead, a second slotted portion is symmetrically disposed about the center plane on the opposite surface of stationary grip 100. Top surface 146 of body section 142 and line SL define an angle θHAN. In one embodiment, angle θHAN may range from about 90° to about 150° to meet ergonomic conditions, and angle θHAN may be about 130° to meet ergonomic considerations. Hole 151 is provided to receive handle pin 132 for connecting pivot grip 110 and stationary grip 100.

As shown in FIG. 4, drill guide assembly 10 is configured in a non-actuated position when pivot grip 110 is at a maximum separation angle, θMAX, from stationary grip 100. This non-actuated position also corresponds to a position in which vertex 152 of actuation bar 310 is located proximal to a user from line EP, where line EP is generally parallel to line SL and defined along the outer edge 154 of grip section 140. Thus, in this non-actuated position, vertex 152 of actuation bar 310 is located proximal to a user with respect to vertex 156 of stationary grip 100. In this position, latch 130 is in a unlatched position and thus not engaged with actuation bar 310.

Figure 5A:
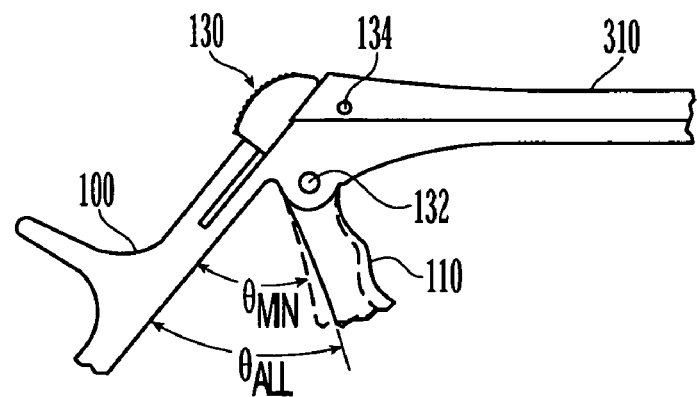

In use, when a surgeon squeezes pivot grip 110 toward stationary grip 100, actuation bar 310 is actuated linearly, toward a distal portion of drill guide assembly 10. As shown in FIG. 5A, when pivot grip 110 reaches a separation angle θALI from stationary grip 100, actuation bar 310 is almost fully actuated, thereby positioning drill guide assembly 10 in an actuated position (further described below). In this position, vertex 152 of actuation bar 310 is generally adjacent line SL, such that side 160 of actuation bar 310 is generally co-linear with edge 144 of grip section 140.

As leaf springs 120 (FIG. 1) bias pivot grip 110 and stationary grip 100 to a non-actuated position, a surgeon must continue to apply pressure to pivot grip 110 urging it toward stationary grip 100 to maintain an actuated position of actuation bar 310. To facilitate easier, more convenient use of drill guide assembly 10, latch 130 preferably is provided to maintain actuation bar 310 in the actuated position, such that pivot grip 110 is maintained separated by an angle θALI from stationary grip 100. This obviates the need for a surgeon to continue to squeeze pivot grip 110 and stationary grip 100 after proper actuation has occurred. Instead, in use, the surgeon's thumb moves latch 130 linearly along stationary grip 100 toward actuation bar 310 and into abutment with face 160 of actuation bar 310, thereby preventing any proximal movement. Latch 130 then remains in place due to the backward pressure generated by leaf springs 120 (FIG. 1) applied to latch 130 through face 160.

Figure 5B:
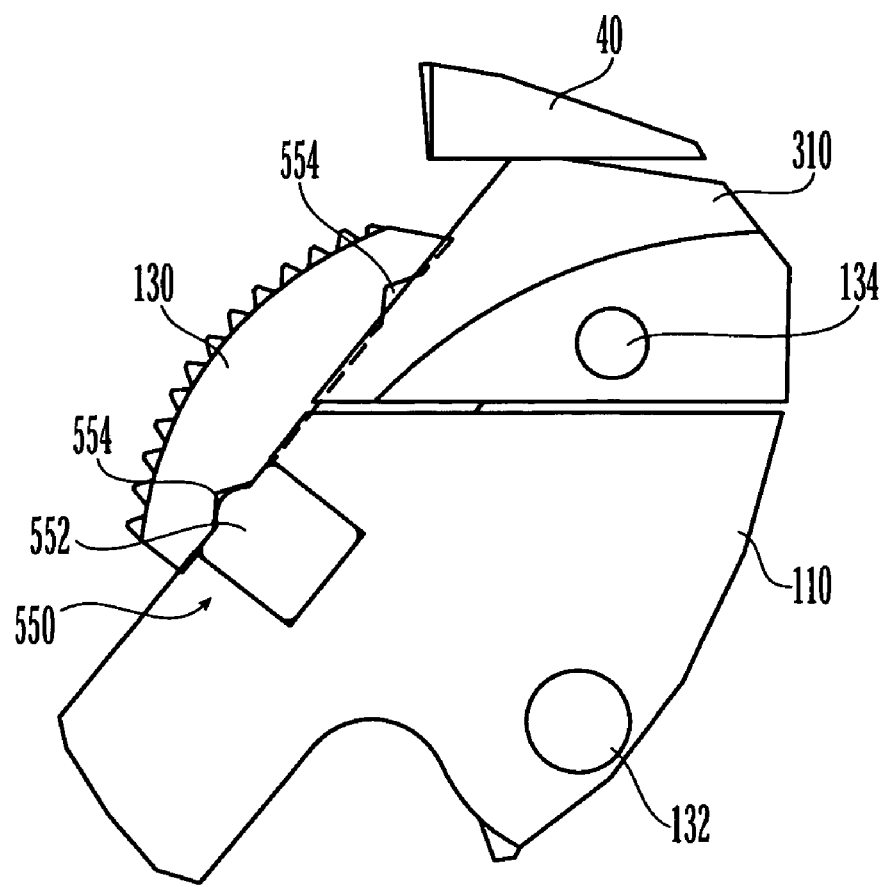
FIG. 5B shows a latch lock of the drill guide of FIG. 1.

According to one embodiment, as shown in FIG. 5B, latch 130 is configured with a ball plunger latch mechanism 550. According to this embodiment, slide latch 130 can be locked in an upward or downward position, (upward referring to a direction away from a user's hand, and conversely, downward referring to a direction toward a user's hand). The ball plunger latch mechanism 550 comprises a spring-biased ball 552 inset within stationary grip 100 and corresponding upper and lower ball receiving recesses 554 in the slide latch 130. In use, when a surgeon actuates the drill guide by squeezing the handles and then moves the slide latch 130 upward to lock actuation bar 310 in place, the ball 552 may resiliently engage the lower recess 554 in latch 130, such that latch 130 will become locked in position. Thereafter, the surgeon can rotate the drill guide assembly 10 in virtually any direction and around virtually every axis and latch 130 will constrain actuation bar 310 in a locked actuated position. Even if the surgeon places a squeezing pressure on pivot grip 110, thereby relieving the back pressure applied to latch 130 from actuation bar 310, latch 130 remains in position. To release the lock, the surgeon can move latch 130 to a downward position, thereby disengaging the ball 552 from the lower recess and resiliently engaging the ball in the upper recess 554 and locking the latch 130 in a downward position so that latch 130 remains out of the working path of actuation bar 310.

In one embodiment, the movement of latch 130 is guided along slotted portions 144, with disengagement from slotted portions 144 prevented by an abutment (not shown) on stationary grip 100. Alternatively, other means of restricting the travel of latch 130 can be used, such as a protrusion on face 160 of actuation bar 310. In one embodiment, latch 130 is also provided with teeth 162 or ridges to enhance gripping of the latch 130 by the surgeon's thumb, thereby facilitating movement of latch 130. Other latch means known in the art, such as pins or ratchet mechanisms are also contemplated and may alternatively be used.

As shown in FIG. 5A, actuation bar 130 may be released from an actuated position by squeezing pivot grip 110 and stationary grip 100 to a slightly smaller separation angle than θALI, such that pivot grip 110 and stationary grip 100 are separated by an angle θMIN. Because actuation bar 310 is moved away from latch 130 when separation angle θMIN is reached, the backward pressure applied by face 160 against latch 130 is diminished, and latch 130 is freely movable to a position that will not engage actuation bar 310.

Advantageously, a surgeon can operate drill guide assembly 10 with only one hand, due to the ergonomic positioning of pivot grip 110 and stationary grip 100. In embodiments which include latch 130 for releasably locking pivot grip 110 and stationary grip 100 with respect to each other, latch 130 is also ergonomically positioned so that one-handed operation of drill guide assembly 10 is convenient.

In the one embodiment, actuating handle 20 can be located remotely from the plate engaging or distal end of drill guide assembly 10, thereby reducing clutter and improving visibility at the surgical site while implanting and affixing a fixation plate.

Referring now to FIGS. 1–5B, a main body 30 of drill guide 10 extends along a longitudinal axis LA. Main body 30 generally provides structural support and stability to drill guide assembly 10 and a means of interconnecting actuating handle 20, guide barrel 40, and the plate engagement and aligning structure 60, as well as for providing support for the optional pivoting mechanisms 50a, 50b.

Main body 30 comprises extension arm 200, which is generally an extension of stationary grip 100. According to one embodiment, extension arm 200 extends between a proximal end 70 and a distal end 80 of drill guide assembly 10 with the proximal end 70 being located generally near actuating handle 20. The distal end 80 extends away from actuating handle 20 so that bushing 60 is located closest to a distal end of drill guide assembly 10 for engagement with a bone plate. It will be appreciated by one of ordinary skill in the art that extension arm 200 can be coupled to stationary grip 100 by a pin assembly, through a screw-in connection, an adhesive bond, welding, laser welding, or the like. Furthermore, the components can be formed integral with each other. Main body 20 also provides for attachment of proximal pivot coupler 52 and bushing 60, (further described below).

Actuation bar 310, as shown in FIGS. 1, 4, and 5A, is generally positioned adjacent extension arm 200 and extends from the proximal end to the distal end of extension arm 200. Actuation bar 310 is coupled near its proximal end to an internal linking member (not shown) through actuation pin 134. The linking member (not shown) interconnects pivot grip 110 at handle pin 132 and actuation bar 310 at actuation pin 134, such that when pivot grip 110 is pivoted toward stationary grip 100, actuation bar 310 is urged toward the distal end of drill guide assembly 10.

Drill guide assembly 10 also includes at least one guide barrel or guide sleeve 40. Guide barrel 40 comprises a hollow tube, and extends substantially linearly along main body 30 from a proximal end to a distal end of main body 30. In use, guide barrel 40 provides a protective barrier within which surgical tools (see FIGS. 21 to 23) may be inserted for particular and precise alignment within a surgical site. Furthermore, due to the length of guide barrel 40 and the fact that guide barrel 40 is substantially a closed tube along its length, soft tissue located between the skin and the surgical site is protected from interaction with the inserted surgical tools. Therefore, the vital organs and/or tissues of a patient are less likely to be inadvertently damaged during installation and removal of the tools used in the surgical procedure. This is especially important for surgical procedures utilizing an anterior approach to the spine because internal abdominal and/or thoracic organs are delicate and may be damaged by even a slight contact with sharp surgical instruments often used in spinal procedures, such as drills, awls, taps, screwdrivers, screws, or the like. In one embodiment, the guide sleeve 40 may be of sufficient length so that at least a portion of the sleeve extends outside of the incision when the drill guide assembly 10 is engaged with a bone plate and the plate is placed on the targeted bone site. According to one embodiment, the guide barrel 40 may be sized and configured to be used a drill guide for vertebral surgical procedures. In an alternative embodiment, the guide barrel 40 may be sized and configured to be used as a drill guide for surgical procedures performed on about vertebra T1 to about vertebra S1. Accordingly, in one embodiment the guide barrel 40 may be from about 50 millimeters (mm) to about 400 mm in length. In another embodiment, the guide barrel 40 may be about 260 mm in length.

Guide barrel 40 has substantially hollow circular cross section, and is sized and configured to receive surgical tools. The surgical tools are precisely received by guide barrel 40 such that the combination drill guide/tool unit produces an accurate and predictable surgical procedure. In alternative embodiments, the inner diameter of guide barrel 40 may be varied depending on the desired surgical procedure and the tools used with that procedure. In one embodiment, the inner diameter of guide barrel 40 may be from about 4 mm to about 15 mm. In an alternative embodiment, the inner diameter of guide barrel 40 may be about 8.2 mm.

Providing a full length guide barrel having the lengths and configurations disclosed above may allow a surgeon to use a single device to perform bone plate placement procedures in various locations in the body and with variously proportioned patients. For example the invention is particularly well suited for use with larger patients, where the distance from the abdominal incision to the surgical site may be significant.

Guide barrel 40 may have an inside diameter sized to slidingly accept various tools used during plate attachment procedures. Examples of such tools are awls, drills, taps, temporary attachment pins, bone screws, and pin placement and screw driving tools.

Guide barrel 40 may also include internal or external stops configured to correspond with stops or surfaces on the tools used with drill guide assembly 10 to limit the distance the tool may protrude from the distal end of guide barrel 40. According to one embodiment, guide barrel 40 (FIGS. 1 and 13) includes stop surface 692 near the proximal end 70 of guide barrel 40. In use, such a stop arrangement may assist a surgeon in drilling, tapping, etc. to a precise and predetermined depth of bone, also, such stop surfaces help ensure that a surgeon does not drill, tap, awl, screw, or the like, too deeply into the bone.

Figure 2:
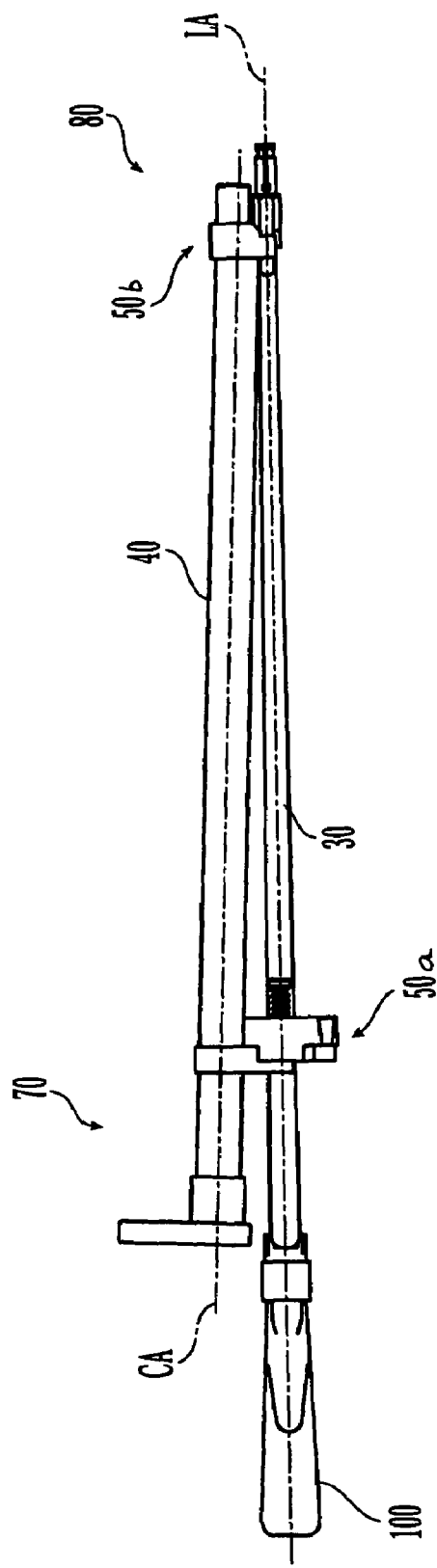
FIG. 2 shows a top view of the drill guide of FIG. 1.

Referring to FIG. 2, which is a top plan view of the drill guide assembly 10 shown in FIG. 1, single guide barrel 40 can be seen positioned generally adjacent main body 30, in a left-handed locked position. In one embodiment, central axis CA of guide barrel 40 is not parallel with longitudinal axis LA of main body 30 when viewed in the medial-lateral plane, as shown in FIG. 2. In one embodiment, central axis CA of guide barrel 40 may be inclined from about 0 degrees to about 8 degrees one either side of longitudinal axis LA of main body 30 when viewed in the medial-lateral plane. Alternatively, in another embodiment, central axis CA of guide barrel 40 may be inclined about 2.15 degrees on either side of longitudinal axis LA of main body 30 when viewed in the medial-lateral plane. In use, the angle of central axis CA of guide barrel 40 is predetermined and is based on the desired angle of implantation for the bone screws to be used to secure the bone plate to the bone, and thus is dependent upon the procedure to be conducted with drill guide assembly 10 and the components to be utilized. In an alterative embodiment, central axis CA of guide barrel 40, when viewed in the medial-lateral plane, may be parallel to the longitudinal axis LA of main body 30.

It should be recognized that accurate and precise alignment and positioning of bone screw holes is important because in many plate designs an improperly aligned screw can cross-thread with the threads of the bone screw holes and destroy the integrity of a locking mechanism associated with a bone plate hole and/or the screw being inserted through the locking mechanism. Furthermore, an improperly implanted screw may affect the longevity of the implanted device. Screws that are placed at improper angles with respect to the bone may loosen over time, thus compromising the integrity of the fixation plate. Accurate and precise placement of bone screws becomes more difficult when the depth of the incision is large, such as with an anterior approach to the lumbar spine, because visibility of the working area may be hindered by tissue, blood, etc. This may be particularly true with larger patients. Thus, providing a drill guide having a predetermined screw alignment trajectory, as disclosed herein, and which also provides maximum protection for the soft tissues bordering the surgical site for patients of all body types, is a distinct advantage both to the surgeon and the patient.

It should be appreciated that the central axis CA of guide barrel 40 and the longitudinal axis LA of main body 30 appears parallel when viewed in the sagittal plane, as shown in FIG. 1. It is also noted that the described relative angles between guide barrel 40 and main body 30 are illustrative only, and one of ordinary skill in the art will recognize that any appropriate angle may be provided, depending upon the surgical procedure to be performed.

Bone plates may be provided with left and right screw hole pairs. Accordingly, the guide barrel 40 may be rotatable or pivotable moved with respect to the longitudinal axis of main body 30 so that a single guide barrel 40 can be selectively positioned in a left and/or a right position, with respect to main body 30, for facilitating access to the left and/or the right bone screw hole of a surgical bone plate. Advantageously, because guide barrel 40 is rotatable, only one guide barrel 40 need be present on drill guide assembly 10 to service a pair of bone screw holes, thereby requiring a smaller working space which corresponds to a smaller surgical site and less potential for soft tissue trauma as compared to devices which use two guide barrels.

Drill guide apparatus 10 further may include proximal and distal pivot mechanisms or pivot couplers 50a, 50b for use in rotatably coupling guide barrel 40 to main body 30 of drill guide assembly 10. Typically, there are two pivot couplers 50a, 50b associated with drill guide assembly 10, one near proximal end 70 and one near distal end 80 of main body 30. Each pivot coupler 50a, 50b includes a pivot pin (further described below), the pivot pins being in substantial axial alignment with each other, thereby forming a pivot axis 699 about which guide barrel 40 can rotate between a left and a right working location with respect to main body 30. (Note: the left working position is shown in FIGS. 1 and 2).

A proximal pivot coupler 52 is located toward the proximal end of drill guide assembly 10, near actuating handle 20. According to FIG. 6, proximal pivot coupler 52 includes a mount 600 for fixed attachment to main body 30, a pivot pin 620, a spring 640, and a swivel link 660.

Figure 6:
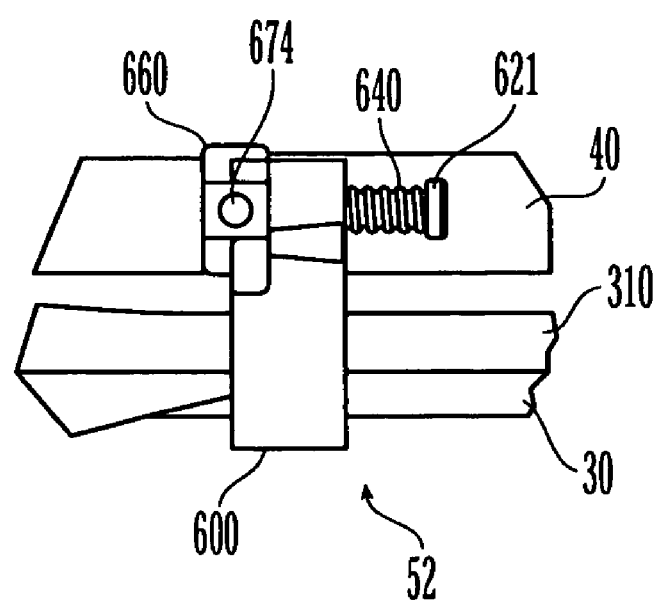
FIG. 6 shows a guide sleeve proximal pivot coupler of the drill guide of FIG. 1.
Figure 7:
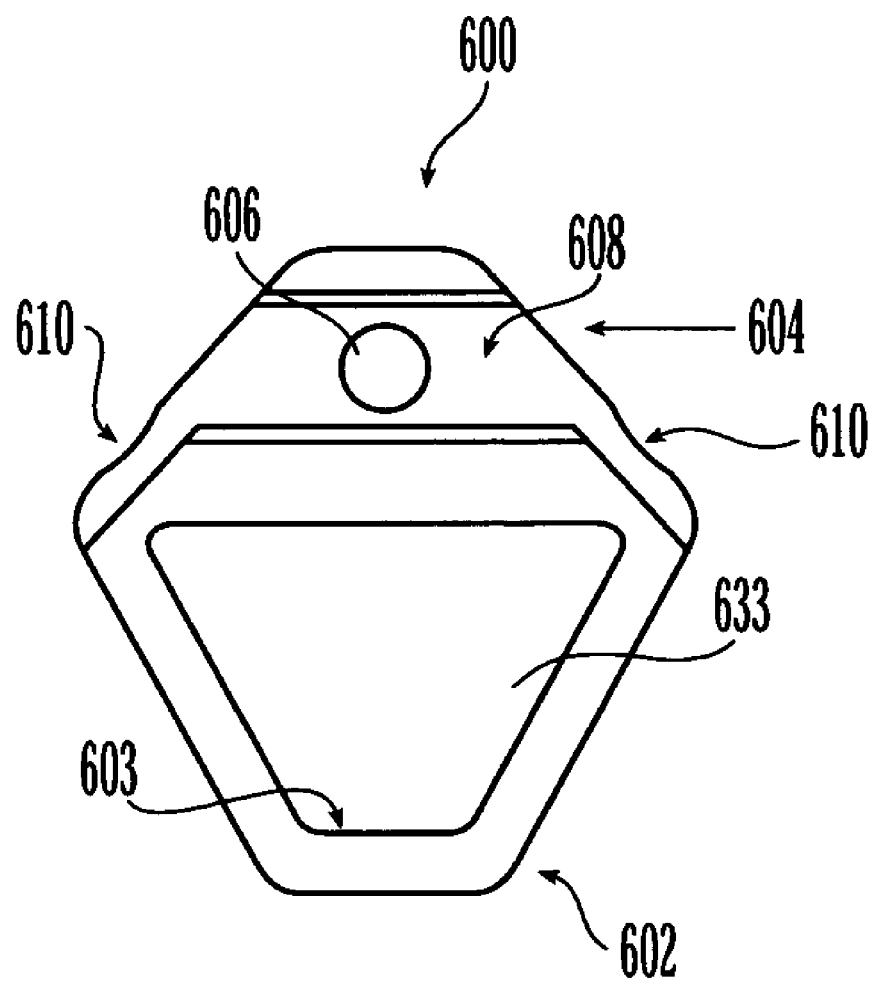
FIG. 7 shows a guide sleeve mount of the drill guide of FIG. 1.
Figure 8:
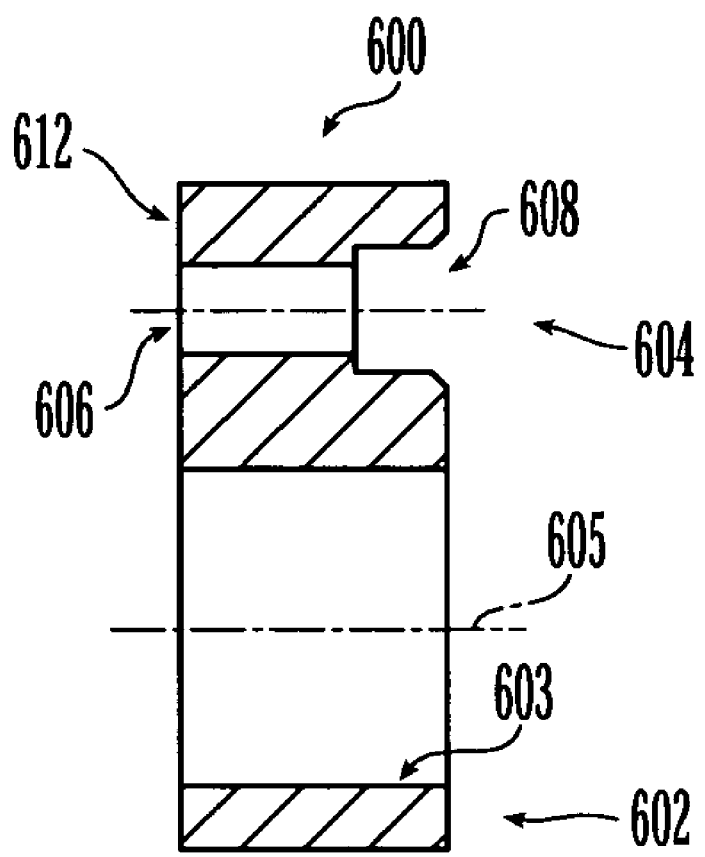
FIG. 8 shows a cross-section of the mount of FIG. 7.

FIGS. 7 and 8 show an embodiment of mount 600. Mount 600 generally comprises an open centered trapezoidal shape 633, configured and sized to accept main body 30 through the open center trapezoidal shape 633 of mount 600. Mount 600 has central axis 605 (FIG. 8) generally parallel to longitudinal axis LA of main body 30. Main body 30 is generally fixedly attached to a first portion 602 of mount 600 along surface 603. Mount 600 includes a second portion 604. Second portion 604 generally includes a pivot pin bore 606, a locking channel 608, and guide barrel seats or radial recesses 610. According to one embodiment, pivot pin bore 606 extends completely through mount 600 and is sized and configured to rotatably receive pivot pin 620. According to this embodiment, pivot pin 620 extends completely through mount 600, being fixedly attached on a proximal end with swivel link 660 (further described below) and freely extending in a distal direction from mount 600 toward the distal end of drill guide assembly 10. In another embodiment, pivot pin 620 can be fixedly attached within pivot pin bore 606 and swivel link 660 can rotatably receive pivot pin 620. Near the distal end of pivot pin 620, pivot pin 620 flares outward, increasing in diameter to form a lip 621 (FIG. 6). In an assembled state, spring 640 is disposed about pivot pin 620 between lip 621 and surface 612 of mount 600; in this manner, spring 640 biases pivot pin 620 distally away from mount 600, which draws the swivel link 660 in close contact with mount 600.

Pivot pin bore 606 is centrally aligned with locking channel 608 on the proximal side of mount 600. FIG. 8 shows a cross-sectional view of mount 600. Locking channel 608 has an axis generally perpendicular to the longitudinal axis of main body 30, and is therefore also perpendicular to the central axis of mount 600. Locking channel 608 is also configured to receive swivel link 660 (further described below).

Mount 600 is further configured with radial recesses 610, configured to receive the outer diameter surface of guide barrel 40 when guide barrel 40 is positioned in a left or a right position.

Figure 9:
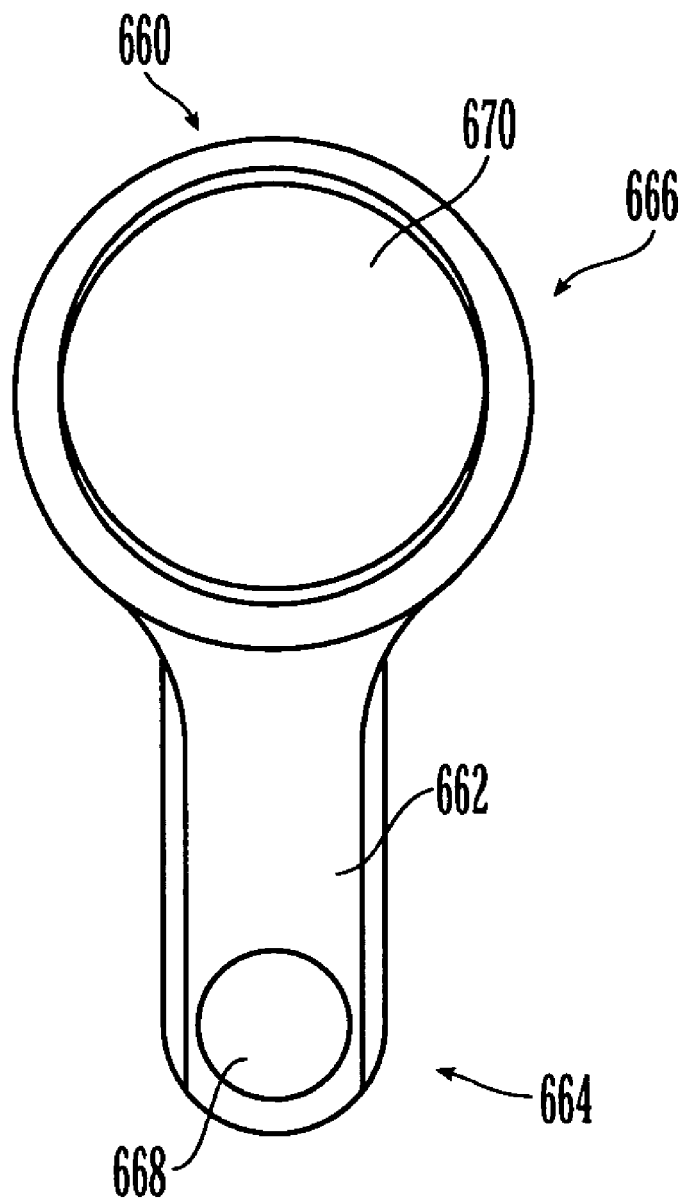
FIG. 9 shows a swivel link of the drill guide of FIG. 1.
Figure 10:
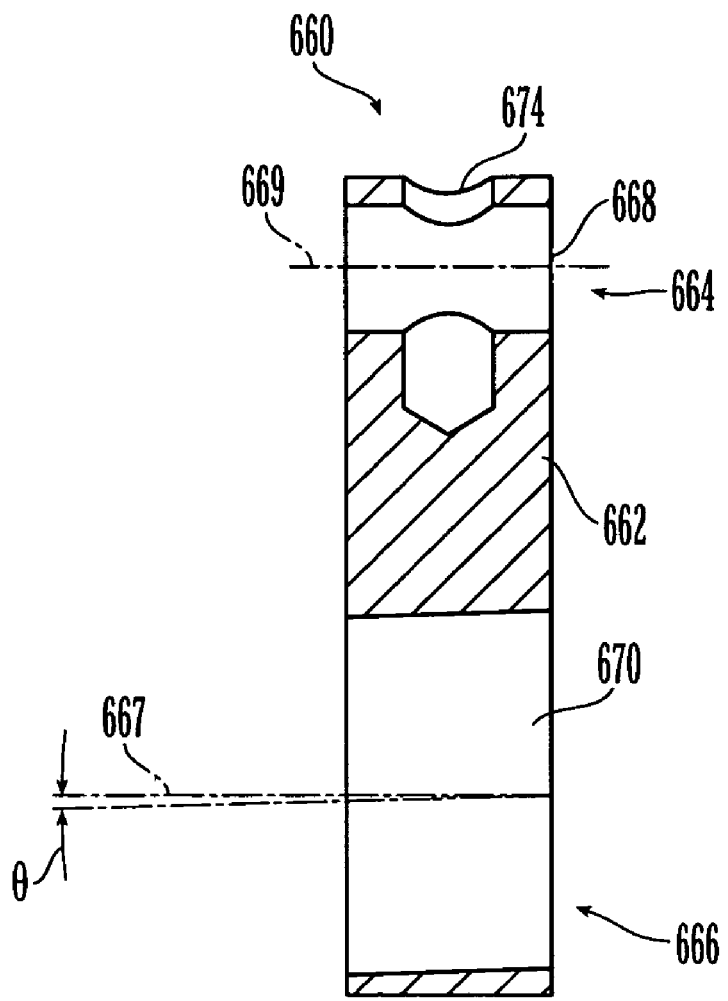
FIG. 10 shows a cross-section of the swivel link of FIG. 9.

FIGS. 9 and 10 show an embodiment of swivel link 660 of the proximal pivot coupler 52. Swivel link 660 rotatably links guide barrel 40 to mount 600, and comprises an elongated body 662 extending between a first end 664 and a second end 666. Swivel link 660 includes two generally circular bores, a first bore 668 located in the first end, and a second bore 670 located in the second end. First bore 668 is sized and configured to receive the proximal end portion of pivot pin 620 which protrudes proximally from mount 600 while second bore 670 is sized and configured to receive guide tube 40. According to one embodiment, pivot pin 620 is fixedly coupled with swivel link 660 by way of press pin (not shown), inserted into cross-bore 674 (FIG. 10). However, it will be appreciated by one of ordinary skill in the art that pivot pin 620 can be attached to swivel link 660 in any appropriate way including screwing, bolting, gluing, bonding, compression fit, press fit, welding, laser welding, or the like. Furthermore, the components can be formed integral with each other.

FIG. 10 shows a cross-sectional view of swivel link 660. As illustrated, the central axis 667 of first bore 668 is not parallel to the central axis 669 of second bore 670, such that the two axes assume an angle $\theta$ with respect to each other. In one embodiment, angle $\theta$ may be about 2.15 degrees. In another embodiment, angle $\theta$ may be from about 0 degrees to about 8 degrees. In use, the angle $\theta$ between the first and second bore axes is predetermined and based on the desired angle of implantation of the bone screws to be used to secure the plate to the bone, and thus is dependent upon the procedure to be conducted with drill guide assembly 10 and the components to be utilized.

As described above, elongated body 662 extends between first bore 668 and second bore 670 of swivel link 660. Elongated body 662 is sized and configured to be received within locking channel 608 of mount 600 when guide barrel is positioned in a left or right position (further described below).

Figure 11:
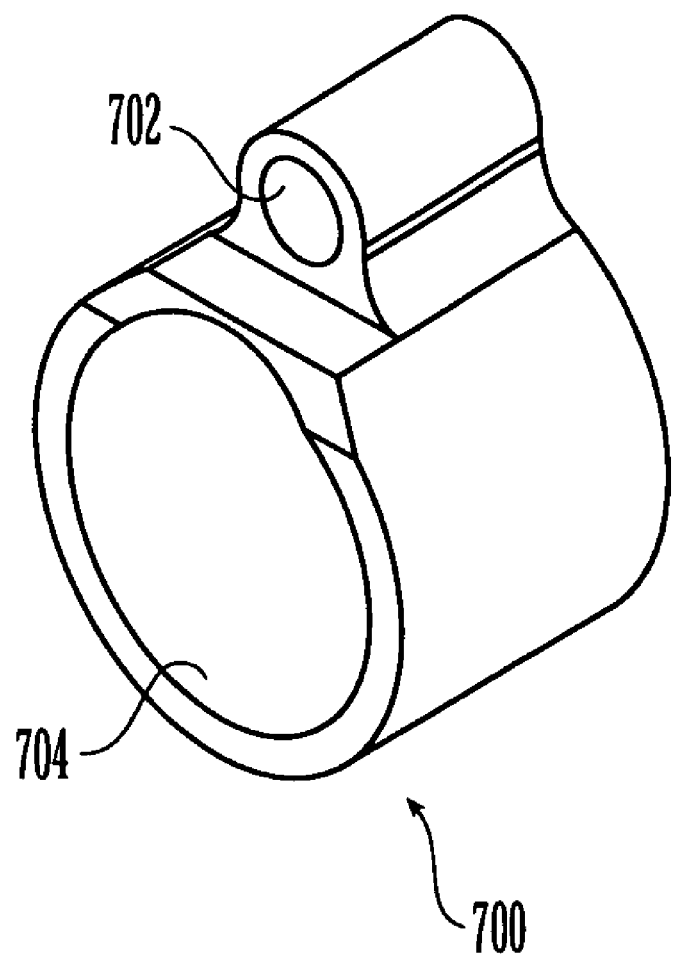
FIG. 11 shows a distal pivot coupler of the drill guide of FIG. 1.
Figure 12:
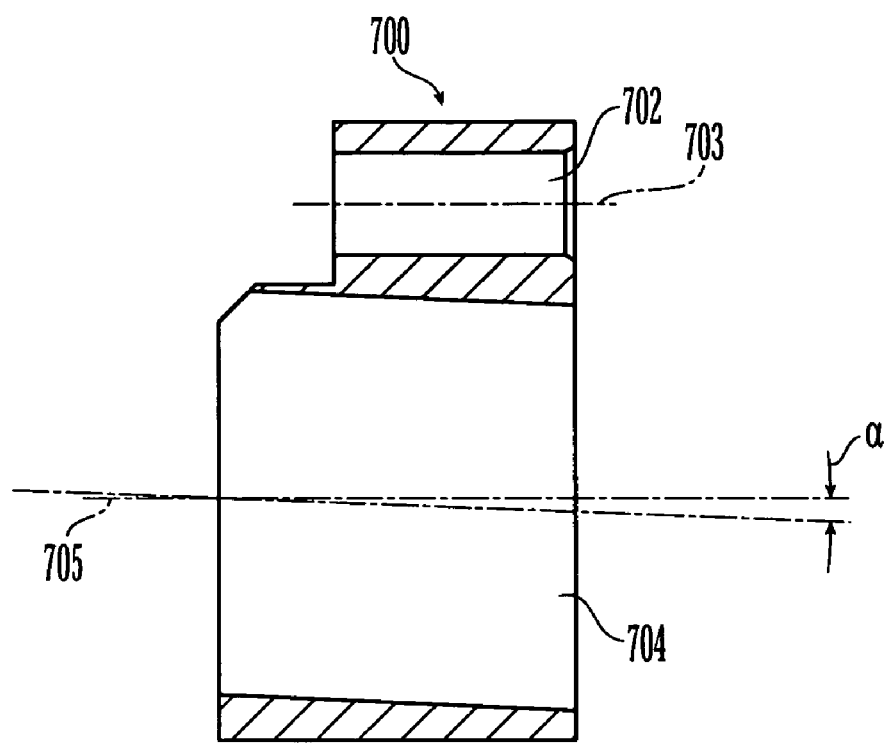
FIG. 12 shows a cross-section of the distal pivot coupler of FIG. 11.

FIGS. 11 and 12 show distal rotatable coupler 700, which rotatably links guide barrel 40 with bushing 60 near the distal end of drill guide assembly 10. Distal rotatable coupler 700 includes a second pivot pin bore 702 and a guide barrel bore 704. Second pivot pin bore 702 is sized and configured to slidably receive a second pivot pin (not shown) to pivotably link the coupler 700 to the distal bushing assembly 60. The central axis of the second pivot pin lies along a longitudinal axis defined by the central axis of pivot pin 620 of proximal pivot coupler 52, such that an axis of rotation is formed whereby guide barrel 40 can rotate about the axially aligned central axes of both pivot pins.

FIG. 12 is a cross-section of distal rotatable coupler 700. As illustrated, the central axis 703 of second pivot pin bore 702 is not parallel to the central axis 705 of guide barrel bore 704, and the two axes assume an angle $\alpha$ with respect to each other, the angle $\alpha$ being the same as that angle between the first central axis 667 and the second central axis 669 of the first and second bores 668 and 670, respectively, of swivel link 660. In one embodiment, angle $\alpha$ may be about 2.15 degrees (as viewed between central axis 703 of second pivot pin bore 702 and central axis 705 of guide barrel bore 704). In another embodiment, angle $\alpha$ may be from about 0 degrees to about 8 degrees. In use, the angle $\alpha$ between the first and second bore axes, 703 and 705, respectively, is predetermined and, coordinated with angle $\theta$ of swivel link 660, is based on the desired angle of implantation for the bone screws to be used to secure the plate to the bone, and thus is dependent upon the procedure to be conducted with drill guide assembly 10 and the components to be utilized.

Figure 13:
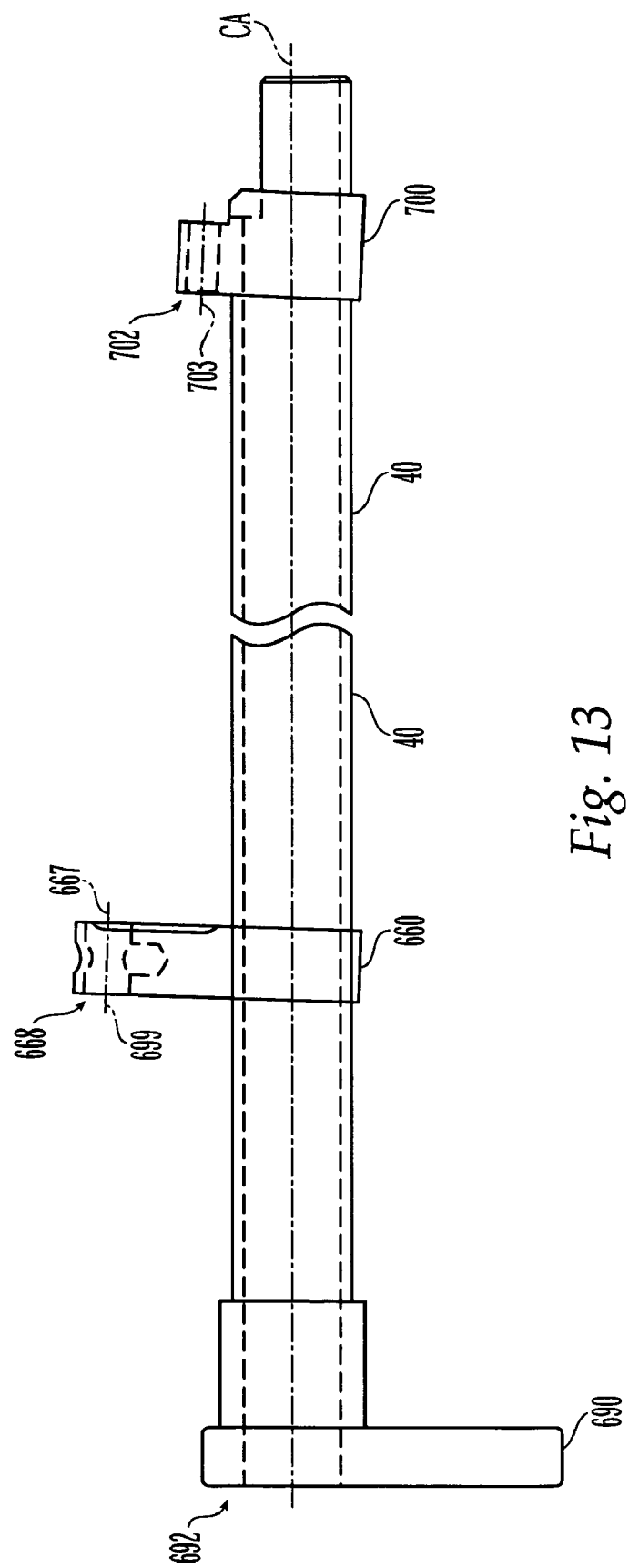
FIG. 13 shows a guide barrel of the drill guide of FIG. 1.

FIG. 13 shows guide barrel 40 with flange 690 and proximal pivot coupler 52 affixed in a proximal position of guide barrel 40 and distal rotatable coupler 700 affixed in a distal position, respectively. Furthermore, guide barrel 40 is affixed to guide barrel bore 704 of swivel link 660 by means such as laser welding, welding, press fit, epoxy bond, screw threads, or the like. Furthermore, the components can be formed integral with each other. As shown in FIG. 13, a central axis CA of guide barrel 40 is not parallel with the axis of rotation formed between the central axis 667 of first bore 668 and the central axis 703 of second pivot pin bore 702 but, as earlier described, is offset by angle $\alpha$. In another embodiment, the central axis CA of guide barrel 40 could be substantially parallel with the axis of rotation formed between the central axis 667 of first bore 668 and the central axis 703 of second pivot pin bore 702 as may be appropriate to suit the needs of a user.

The operation of swiveling or rotating guide barrel between a left and a right position, with respect to the longitudinal axis of main body 30, will now be described with respect to one embodiment of the present invention. In use, to rotate guide barrel from one working position (a left or a right position) to the opposite working position, a surgeon may grasp flange 690 toward the proximal end of guide barrel 40 and applying a pulling force. This moves guide barrel 40 in a proximal direction. Because swivel link 660 is fixedly attached to guide barrel 40, swivel link 660 moves proximally pulling pivot pin 620 along with it and compressing spring 640 between the pivot pin lip 621 and mount 600. Furthermore, distal rotatable coupler 700, being fixedly attached to guide barrel 40, also moves proximally with guide barrel 40. The pivot pin (not shown) extending through pivot pin bore 702 of distal rotatable coupler 700 is of sufficient length that it does not become disengaged from pivot pin bore 702. Following sufficient pulling, elongated body 662 of swivel link 660 becomes disengaged from locking channel 608. Assuming guide barrel 40 originated in a left working position with respect to main body 30, the surgeon can then apply a rotational force to guide member 40 in a clockwise direction to urge guide barrel 40 to a right working position. Following rotation of guide barrel 40 about approximately 180 degrees, the surgeon can release guide barrel 40, whereupon spring 640 urges guide barrel 40 in a distal direction, and elongated body 662 reengages with locking channel 608. Guide barrel 40 can be returned to a left working position in the same manner, however, a rotational force in the counterclockwise direction would be applied to guide barrel 40 to rotate guide barrel 40 from a right working position to a left working position with respect to main body 30.

Figure 19:
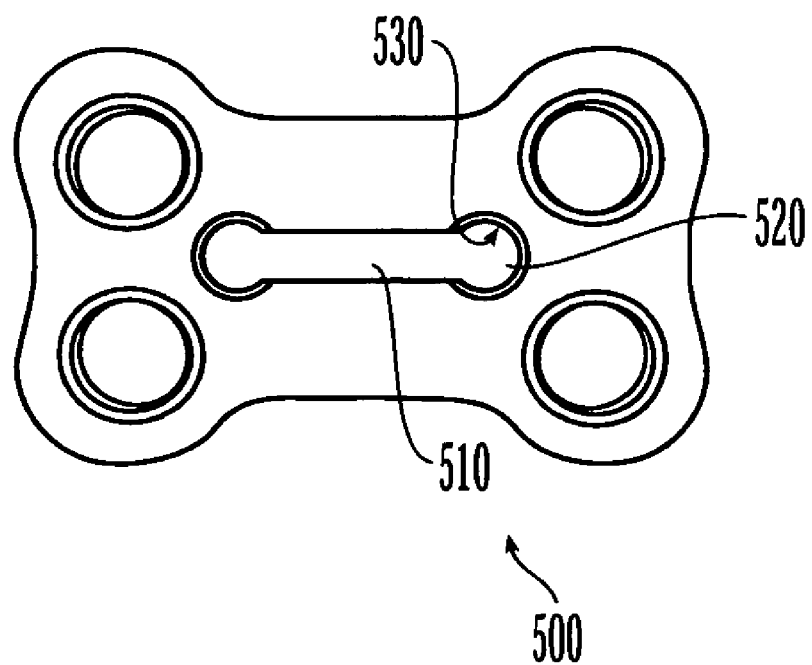
FIG. 19 shows an example of a bone plate that can be used in conjunction with the drill guide of FIG. 1.

Bushing 60 is located toward the distal end of drill guide assembly 10, and provides a coupling mechanism between main body 30, guide barrel 40, and the associated bone plate (FIG. 19). In use, actuation handle 20 causes an engaging portion of the bushing to grip the plate such that guide barrel 40 is aligned with a first bone screw hole of the plate.

Figure 14:
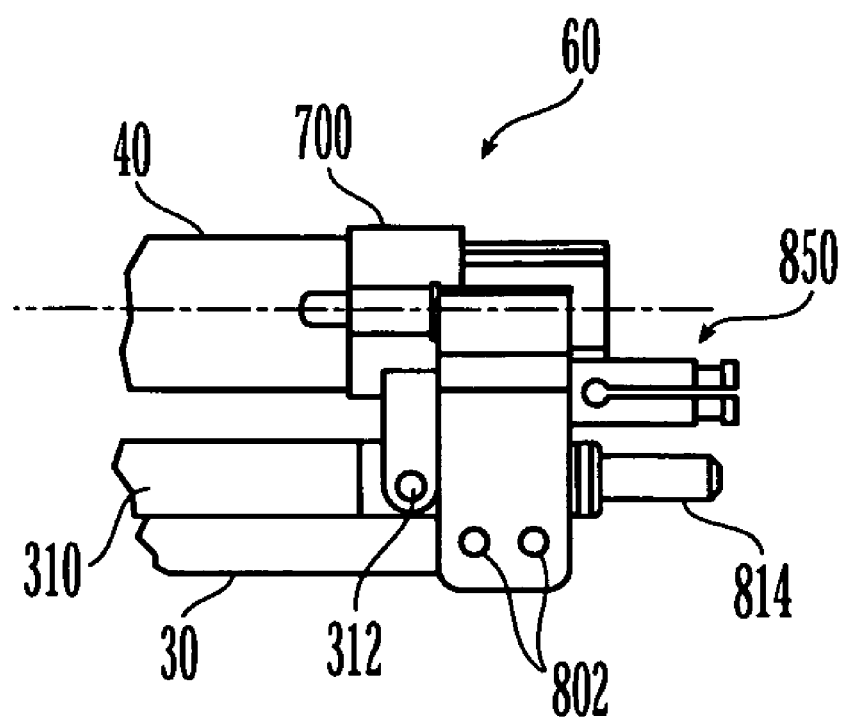
FIG. 14 shows a bushing assembly of the drill guide of FIG. 1.

FIG. 14 shows one embodiment of bushing 60. Bushing 60 is rigidly coupled to main body 30 through two pins 802 located on a lower portion of the bushing, where an upper portion of the bushing comprises a pivot pin bore 810 sized and configured within bushing 60 to fixedly receive the second pivot pin of distal rotatable coupler 700. In one embodiment, the second pivot pin is fixedly attached with bushing 60 by means such as laser welding, welding, press fit, epoxy bone, screw threads, or the like. Furthermore, the components can be integral with each other. Bushing 60 is oriented substantially perpendicular to the longitudinal axis of main body 30.

Figure 15:
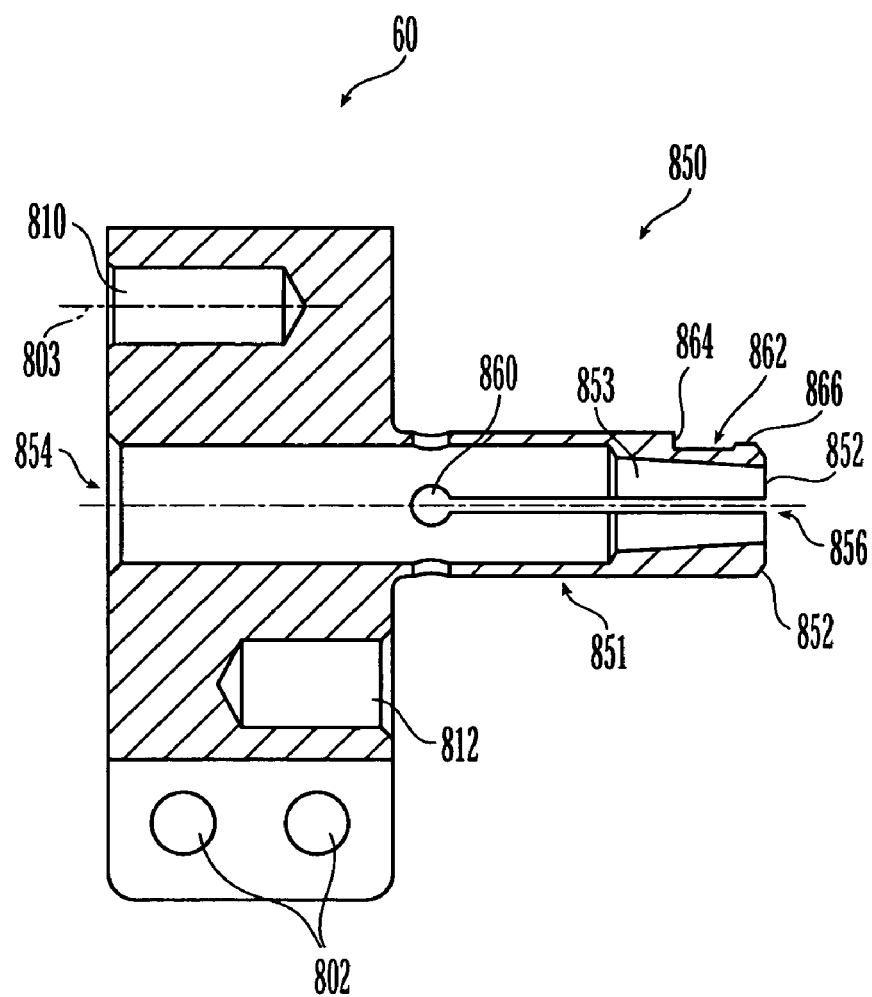
FIG. 15 shows a cross-section of the bushing assembly of FIG. 14.
Figure 16:
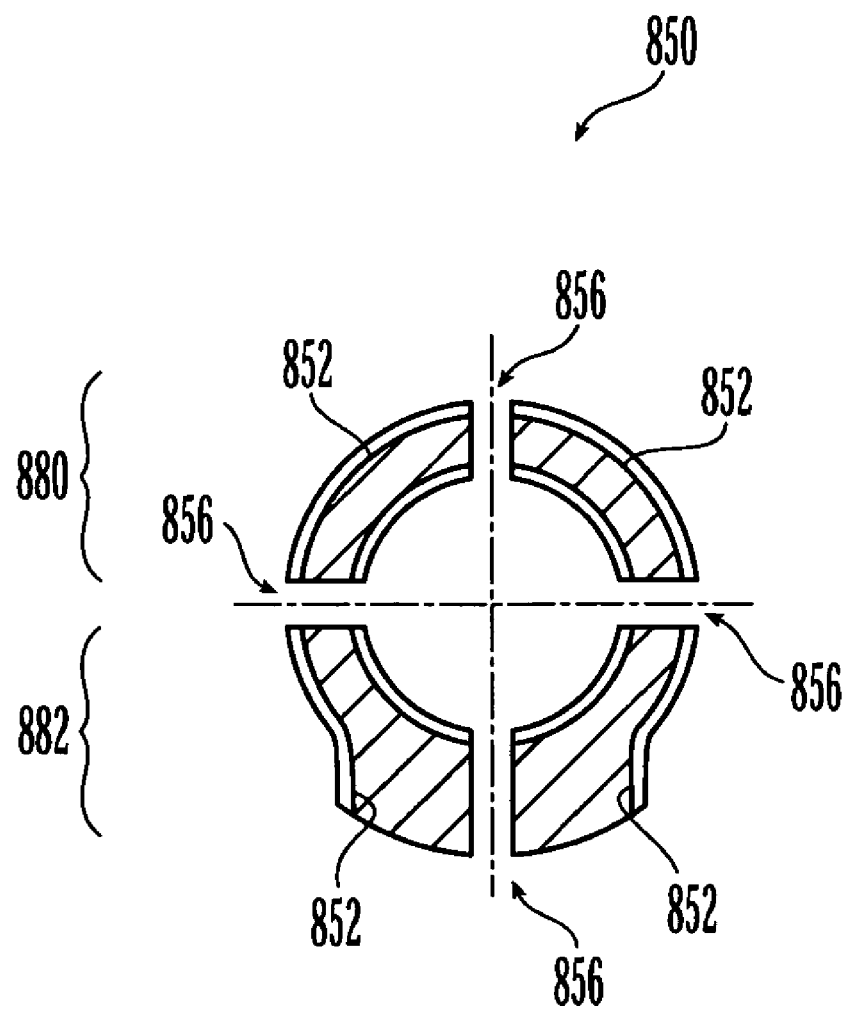
FIG. 16 shows an engagement member of a bushing of the drill guide of FIG. 1.

In one embodiment, as shown in FIG. 15, bushing 60 contains two partial bores; a pivot pin bore 810 and a locator pin bore 812. Pivot pin bore 810 is configured to fixedly receive the second pivot pin, as described above. Thus, guide barrel 40 and distal rotatable coupler 700 rotate about central axis 803 of pivot pin bore 810. It will be apparent to one of ordinary skill in the art that in another embodiment, the second pivot pin can be fixedly attached to distal rotatable coupler 700 and slidably and rotatably received by bushing 60. Furthermore, bushing 60 includes a plate attachment mechanism 850 comprising a cylindrical engaging member 851 that extends distally from the body of the bushing 60. The cylindrical engaging member 851 comprises a plurality of longitudinally extending fingers 852, as shown in FIG. 16. The longitudinally extending fingers 852 are sized and configured to selectively engage a substantially circular portion 520 of a bone plate slot 510 (FIG. 19), as discussed in further detail below.

Bushing 60 further includes a locator pin bore 812 which, along with locator pin 814 is used to rotationally align the drill guide with the bone plate. Locator pin 814 (FIG. 14) may be fixed within locator pin bore 812. It will be appreciated by one of ordinary skill in the art that locator pin 814 can be fixedly attached within locator pin bore 812 by threads, a press fit, epoxy bond, welding, laser welding, or the like. Furthermore, the components can be formed integral with each other. Locator pin 814 extends distally from bushing 60 toward the bone plate to be engaged. In use, the distal end of locator pin 814 is sized and configured to engage a slot 510 formed in a bone plate, such as bone plate 500 shown in FIG. 19. In use, locator pin 814 is slightly smaller than slot 510 of bone plate 500 such that locator pin 814 may be easily received within slot 510 while still minimizing or eliminating rotation of the bone plate with respect to drill guide assembly 10. When locator pin 814 is engaged within the slot in the bone plate, drill guide assembly 10 is both rotationally aligned and rotationally fixed with respect to the bone plate, as described in more detail below.

FIG. 15 shows a cross-sectional view of bushing 60. The plate attachment mechanism 850 generally comprises a taper pin bore 854 and a plurality of distally extending fingers 852 protruding from bushing 60. The distal end of fingers 852 are sized and configured to engage the circular portion 520 of bone plate slot 510 (FIG. 19).

Figure 17:
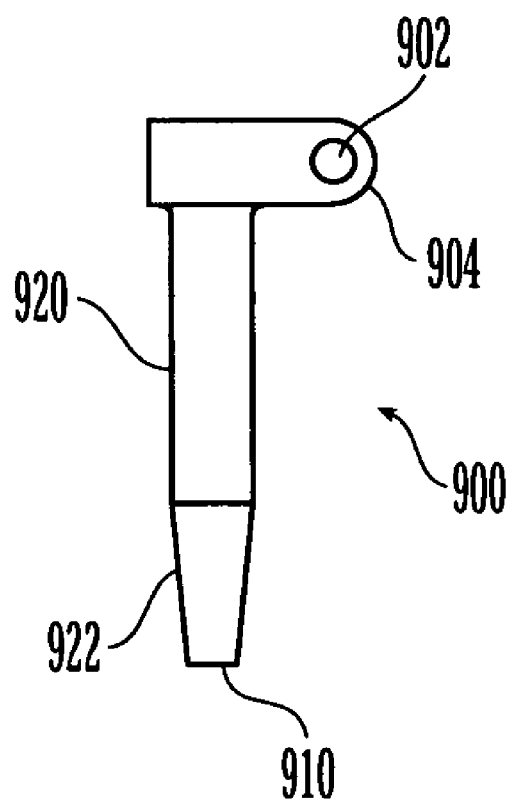
FIG. 17 shows a taper pin of the drill guide of FIG. 1.

Taper pin bore 854 extends through bushing 60 from a proximal side to a distal side of bushing 60 and is sized and configured to receive taper pin 900 (FIG. 17). That is, the taper pin bore approximates the outside diameter of the taper pin, and has a correspondingly tapered bore area 853 located at a distal portion of taper pin bore 854. The taper pin bore is sized to slidingly accept the taper pin 900.

The plate attachment mechanism 850 comprises distally extending fingers 852. In the embodiment illustrated in FIG. 16, four fingers are provided, however, any appropriate number of fingers may be used. Fingers 852 are separated by slits 856 which extend longitudinally between adjacent fingers 852, (see FIGS. 15 and 16). Slits 856 each terminate at a proximal end in a circular cutout 860 (FIG. 15) that serves to minimize stress concentrations in bushing 60 when fingers 852 are expanded radially outward during plate locking actuation. Fingers 852 naturally assume an inward disposition when in a relaxed state, i.e., when actuation handle 20 is in a non-actuated state and the taper pin 900 (FIG. 17) is in a proximal position within taper pin bore 854. In this proximal position, the cylindrical portion 920 and tapered portion 922 of the taper pin 900 reside within the correspondingly shaped portions of the taper pin bore 854.

Figure 20:
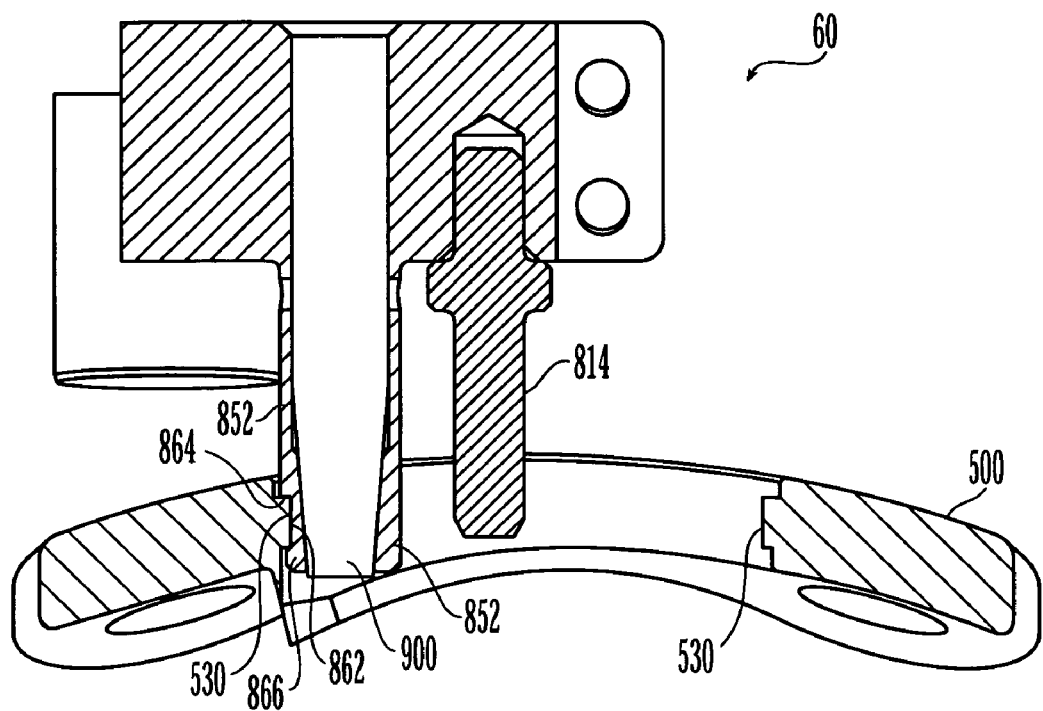
FIG. 20 shows an example of the bushing assembly of FIG. 14 engaged with the bone plate of FIG. 19.

Near the distal-most end of plate attachment mechanism 850, fingers 852 form a radially expandable circumferential neck 862. At the proximal-most portion of neck 862 is a shoulder 864. In one embodiment, a radially expandable rim 866 is formed at the distal-most end of plate attachment mechanism 850, adjacent to neck 862. Neck 862, rim 866, and shoulder 864 may cooperate to define a plate engaging surface, such that when the plate attachment mechanism 850 engages the circular slot portion 520 of bone plate 500, the plate is held between shoulder 864 and rim 866. FIG. 20 shows one embodiment of distally extending fingers 852 engaged within a circular slot portion 520 of a bone plate. In one embodiment, the outside diameter of neck 862 is approximately the same as the inside diameter of circular slot 520, and the length of neck 862 is slightly less-than the thickness of plate 500 such that neck 862 firmly engages a collar 530 within circular slot portion 520.

Alternatively, no rim 866 may be used. For example, in an embodiment without a rim 866, neck 862 can be tapered and the distal-most portion of neck 862 may have a smaller diameter than the portion of neck 862 adjacent shoulder 864. Thus, such a tapered neck may expand within a similarly tapered slot or hole in a bone plate, such as circular slot portion 520 shown in FIG. 19, to provide firm fixation of the bushing 60 with bone plate 500. The several portions of bushing 60, i.e., neck 862, shoulder 864, rim 866, and the like may comprise a single piece of unitary construction. It will be appreciated by one of ordinary skill in the art, however, the several components of bushing 60 can be separate component parts affixed together to form bushing 60. The several components can be affixed together by press fit, epoxy bond, welding, laser welding, or the like. Furthermore, the components can be formed integral with each other. In one embodiment, the center axis of plate attachment mechanism 850 is substantially parallel to the center axis of locator pin 814, both of which are substantially perpendicular to the longitudinal axis of bushing 60 and substantially parallel to the longitudinal axis of main body 30.

According to one embodiment the distal end of fingers 852 may be symmetrically key-shaped, as shown in FIG. 16, and configured and dimensioned to fit and expand within a similarly configured and dimensioned slot (not shown) in a bone plate (not shown). The distal ends of fingers 852 may be configured to have at least one substantially rounded portion 880 and at least one relatively straight portion 882. As shown in FIG. 16, which is a cross-section through neck 862, neck 862 has a C-shaped rounded portion 880 and a Y-shaped portion 882, with four quadrants defined by slits 856. The generally C-shaped rounded portion 880 is configured to be received by a corresponding rounded portion of the bone plate slot 520 (FIG. 19) and the generally Y-shaped portion is configured to be received at least partially into the straight portion of slot 510 (FIG. 19) of the bone plate.

Those skilled in the art will recognize that the neck and rim of the bushing need not be key-shaped. Other appropriate shapes include a cruciform, T-shape, or figure-eight shape, although still other shapes may be used. Such a bushing geometry is appropriately used with at least one correspondingly shaped slot in a bone plate, which is configured and dimensioned to receive the bushing and permit the bushing to align and lock to the bone plate. In the case of a bone plate with a slot that has a shape that is substantially without a straight section, such as a figure-eight shape, a neck 862 may still be used. Because the transition between the lower straight section and the upper arcuate or V-shaped section in a Y-shaped neck can be formed as a sharp transition, a key-shaped neck 862 may still be used to create an effective locking engagement between a neck 862 and a figure-eight shaped slot. The slot also has a shape distinct from the shape of the bone plate fastener holes, such that a surgeon does not mistakenly engage bone plate attachment mechanism 850 to a bone screw hole and inadvertently perform an incorrect procedure on a bone. The keyed bushings, as described, may be used either with or without a locator pin 814, as the keyed geometry of the bushing may provide both the alignment and rotational locking function of the locater pin.

The size and configuration of neck 862 and rim 866 permit a surgeon to insert and remove rim 866 of plate attachment mechanism 850 through a bone plate slot 510, 520 without rim 866 interfering with the bone side of the bone plate. Thus, the length of the neck 862 and rim 866 is less than the thickness of the bone plate 500 such that the plate attachment mechanism 850 does not protrude entirely through the bone plate 500, as shown in FIG. 20. This minimizes the chance that the distal end of the plate attachment mechanism 850 will become pinched between the bone and bone interface surface of the bone plate when the bone plate is screwed to the bone. The plate attachment mechanism is also sized and configured so that when the taper pin 900 is in the non-actuated position the outer diameter of the plate attachment mechanism 850 is sufficiently less than the inner diameter of the slot 520 in the bone plate 500 so that bushing 60 will easily disengage from the bone plate following use. At the same time, rim 866 provides the surgeon with tactile feedback, i.e., a 'click' when rim 866 has completely passed through circular slot 520 in the bone plate and neck 862 engages collar 530, as shown in FIG. 20. Thus, the surgeon has assurance that the mechanism is engaged. In alternative embodiments, rim 866 may be eliminated.

As shown in FIG. 17, taper pin 900 is configured and dimensioned to be slidably received within taper pin bore 854 of bushing 60. According to one embodiment, taper pin 900 is coupled to actuation bar 310 via a pin 312 (FIG. 14) that extends through a pin bore 902 in taper pin 900 and a corresponding bore in actuation bar 310. Parallel and symmetrical flanges 904, with holes 902 together define a gap (not shown) that receives actuation bar 310. A bore in the distal end of actuation bar 310 corresponds to pin bore 902 for receiving pin 312 therethrough and coupling taper pin 900 with actuation bar 310.

When assembled, taper pin 900 extends into taper pin bore 854. In its unactuated state, taper pin 900 extends distally into taper pin bore 854 just proximal to engagement with fingers 852, such that tip 910 of taper pin 900 is housed fully within taper pin bore 954 of bushing 60. According to one embodiment, the taper pin 900 has a cylindrical section 920 and a tapered, conical section 922 to correspond with similar inner profiles within taper pin bore 854. In use, when bushing 60 is placed in a bone plate slot and actuation bar 310 is actuated such that the almost fully actuated position is reached (i.e. when pivot grip 110 is separated by an angle θALI from stationary grip 100), tip 910 is moved toward the distal end of the plate attachment mechanism 850 until it becomes flush with the distal end of fingers 852. As tip 910 is moved further through taper pin bore 854 (by further squeezing together of the handles), taper portion 922 engages the inner diameter of taper pin bore 854 and expands fingers 852 radially outward, thereby gripping and engaging fingers 852 within the circular portion 520 of the bone plate slot 510.

Alternate embodiments of taper pin 900 include an elongated sharpened tip 910 that may engage the bone underlying the bone plate when fully actuated to facilitate drill guide and bone plate alignment. In addition, other shapes of taper pins may be used, such as a non-tapered cylindrical pin or a pin with a spherical protrusion at its distal end. Furthermore, in embodiments of drill guide assembly 10 that have a distal portion of the plate attachment mechanism 850 without a rim 866, and a taper pin without a protruding tip, the slot in the bone plate need not be a through-slot. Thus, the slot may only be a partial channel in the plate sufficient to allow the bushing to engage the plate. In addition, the channel walls may be configured to facilitate positive locking of the bushing to the plate by engaging corresponding radial or linear teeth or grooves between the plate attachment mechanism 850 and bone plate 500. In another alternate embodiment, a rim may be provided on the bushing, and may be configured and dimensioned to fit within a groove formed in the internal surface of the slot or in the channel walls. Other configurations of the bore, pin and bushing will be apparent to one of ordinary skill in the art.

When taper pin 900 is in the actuated, or distal position as shown in FIG. 1, fingers 852 are configured in an expanded position. In this configuration, bushing 60 is engaged with bone plate 500. Only a short travel of pivot grip 110 is required to expand and contract fingers 852 of bushing 60. According to one embodiment, when fingers 852 are in a relaxed or initial position, the external diameter of fingers 852 is slightly smaller than the inside diameter of the bone plate slot configured for receiving fingers 852. Thus, when fingers 852 are in the initial position, the bushing 60 can be easily inserted and removed from the bone plate slot with little or no interference with the slot. Accordingly, in one embodiment, when fingers 852 are in an initial position the outside diameter of neck 862 may be from about 0 mm to about 0.5 mm smaller than the inside diameter of the bone plate slot configured for receiving neck 862. In another embodiment, when the fingers 852 are in an initial position the outside diameter of neck 852 may be about 0.1 mm smaller than the inside diameter of the bone plate slot sized and configured to receive neck 862.

Before and during bone plate implantation, the surgeon may insert the expandable fingers 852 of bushing 60 into a bone plate slot. By squeezing handle assembly 20, the surgeon may thus grasp and manipulate the bone plate. Friction between the distally moved conical section 920 of taper pin 900 and the inner surface of fingers 852, especially at neck 862 and rim 866, may be sufficient to retain bushing 60 in its expanded position and prevent movement between the plate and the drill guide. Thus, when bushing 60 is in the expanded position in a bone plate slot, plate motion relative to the guide during the surgical procedures can be minimized. Furthermore, with locator pin 814 received in a bone plate slot, rotational forces generated during drilling, screwing, or the like, are resisted. Plate motion may be further minimized by the additional use of a taper pin 900 having a pointed tip 910, such that the tip slightly engages the bone and thus serves an additional anchoring function.

Figure 18:
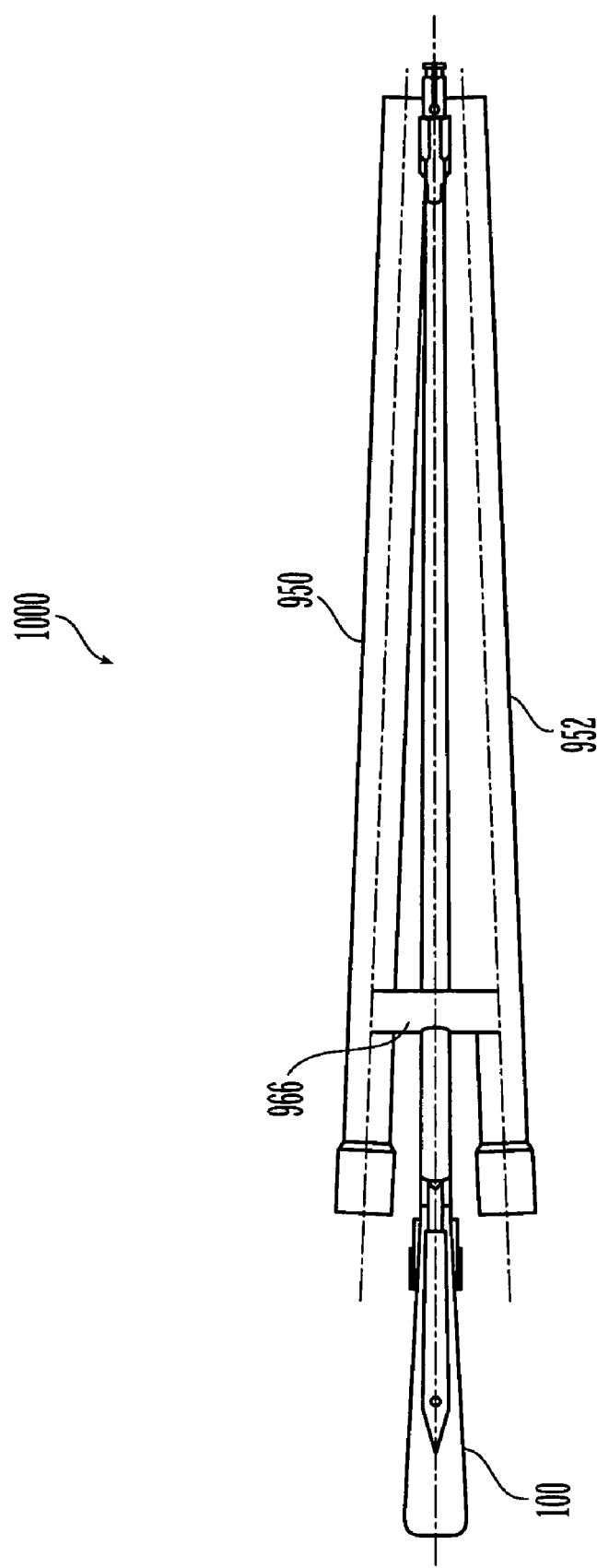
FIG. 18 shows a top view of a drill guide according to another embodiment of the present invention.

According to another embodiment of the present invention, a drill guide assembly 1000 may be provided with two drill guide sleeves, as shown in FIG. 18. The drill guide of this embodiment comprises all of the features, elements, and advantages of the single-barrel design, with the exception that the guide barrel pivoting mechanism are replaced by fixed connections. Thus, for a detailed description of the individual elements of the drill guide of this embodiment, reference should be made to the description of the corresponding elements provided in relation to the single-barrel drill guide 10. According to the present embodiment, the drill guide assembly 1000 couples with a bone plate as described above with a bushing 60 (FIGS. 14 and 15) having expandable fingers 852 (FIG. 15) activated by taper pin 900 (FIG. 17) to engage a first portion of a bone plate slot 520 (FIG. 19) and locator pin 814 (FIG. 14) further disposed to engage a second portion of the bone plate slot 510 (FIG. 19). The dual guide sleeves 950 and 952 may be coupled to main body 30 (FIG. 1) by at least one coupling bracket 960. The coupling bracket 960 couples to main body 30 (FIG. 1) and to each of guide sleeves 950 and 952. The guide sleeves 950 and 952 are configured to align with bone screw holes in a bone plate when bushing 60 is coupled with the bone plate. Thereafter, a surgeon can perform the requisite drilling, tapping, and screw placement procedures through the guide sleeves 950 and 952, respectively, without inadvertently inflicting soft tissue damage to the patients organs or tissues. Furthermore, the length of both guide sleeves 950 and 952 may be greater than the distance between the targeted vertebra and the patient's skin surface, thereby reducing the potential for bone debris to be deposited within the body during bone plating procedures. Thus, a cleaner and safer surgical procedure is ensured with less chance of complication to the patient.

According to one embodiment, the components of surgical drill guide assembly 100 are metallic, passivated, and electropolished. The components are formed of stainless steel, titanium, titanium alloy, or the like, except for the springs which are formed of spring steel. According to one embodiment, the handle member is forged, while the other components are machined, and the surgical drill guide assembly has a matte finish so that the surfaces of the components do not reflect operating room light in such a manner as to distract the surgeon. Some components may be subjected to heat treatments so that the surfaces are work hardened. The surfaces are burr-free. Thus, such a surface finish allows individual components to move with respect to each other in a smooth and non-binding fashion through each component's entire range of motion. Additionally, all pins and fasteners are flush with the surfaces into which they are fixed.

The present invention also involves a method of drilling holes in cervical vertebra. A surgeon may insert the bushing of the drill guide assembly of the present invention into a bone plate slot, align the locator pin in the corresponding plate slot, and thereafter squeeze the actuator handle to slide the taper pin forward, expanding the bushing with the conical portion of the taper pin and locking the drill guide assembly to the plate. The surgeon may then lock the bushing to the plate by locking the taper pin and bushing in fixed relation to each other by manipulating a thumb lock, thus relieving the surgeon of the need to continually squeeze the handle. Thereafter, the surgeon may manipulate the bone plate using the handle, to position the plate at the surface of the targeted bone site without the need for additional plate holders or other tools. The surgeon may then swivel the guide sleeve to the desired left or right position to perform a desired surgical task (i.e., drill a bone hole, screw in a screw, or the like) and lock an elongate member into a locking channel. The surgeon may then align the surgical drill bit along the drilling axis defined through the center of the bore in the guide sleeve and insert the drill bit in the sleeve. The surgeon may then drill a first hole coaxial with the central axis of a first fastener hole in the plate. The surgeon then unlocks the guide sleeve from a locked left or right position by first sliding the thumb lock. Next, to swivel the guide barrel from a left to a right position the surgeon provides a force to overcome a force of a spring retaining the elongate member into the locking channel. The surgeon then swivels the guide sleeve to the other of the left or right positions and releases the guide sleeve, whereby the spring engages the elongate member within the locking channel. The surgeon then performs drilling similar to that described for the first position of the guide tube. In addition to drilling, the holes may be tapped using taps that are extended through the alignment guide sleeve. Each bone screw may be installed in a fastener hole in the bone plate while extending a suitable instrument, along with the bone screw, through the alignment sleeve. The surgeon may unlock the bushing from the plate, open the handle of the drill guide to contract the bushing from the slot, and then freely and unfetteredly remove the drill guide assembly from the plate. In another embodiment, after the surgeon drills bone screw holes, the surgeon may tap and/or implant the screws within that hole before unlocking and swiveling the guide sleeve to the next position.

Figure 21:
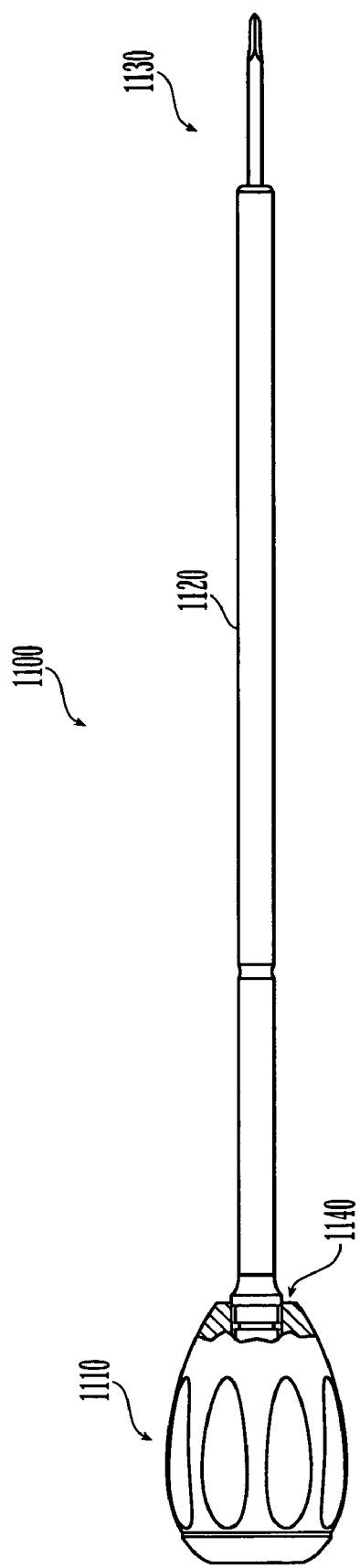
FIG. 21 shows an example of an awl that can be used with the drill guide of FIG. 1.

FIG. 21 shows an awl according to one embodiment of the present invention that is used in conjunction with drill guide assembly 10. Awl 1100 has a handle 1110, main shaft 1120, and bone piercing portion 1130. Handle 1100 may be sized and configured to be gripped by a surgeon for manipulating awl 1100. Main shaft 1120 may be sized and configured to slidably fit within the inner diameter of guide barrel 40. The outer diameter of awl 1100 is slightly smaller that the inner diameter of guide barrel 40 such that awl 1100 is slidably received within guide barrel 40. Awl 1100 can move linearly along and rotate about central axis CA of guide barrel 40. Awl 1100 also comprises a stop 1140 for interaction against flange 690 (FIG. 13). In use, stop 1140 abuts stop surface 692 of flange 690 when a surgeon inserts awl 1100 to a predetermined depth into guide barrel 40. The stop 1140 and stop surface 692 can be sized and configured to limit the amount of protrusion of awl 1100 from the distal end of guide barrel 40, thereby improving safety to a patient by limiting the depth awl 1100 can be inserted into the bone.

Figure 22:
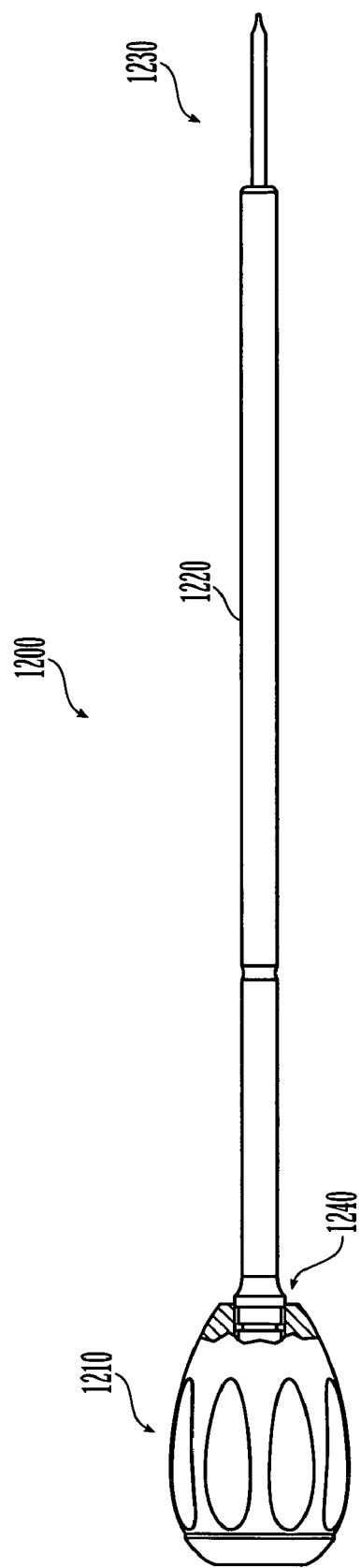
FIG. 22 shows an example of a fixation pin that can be used with the drill guide of FIG. 1.
Figure 23:
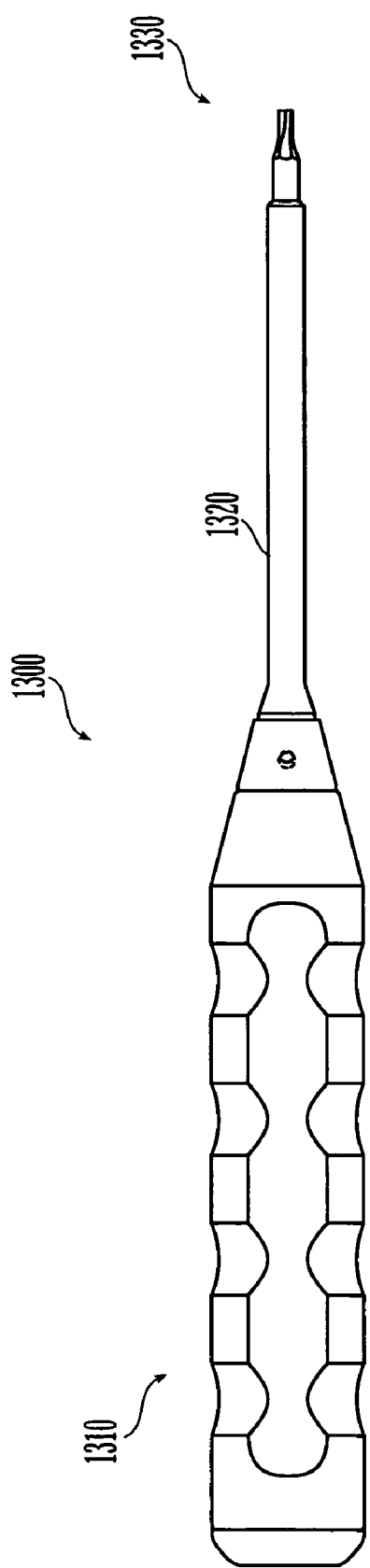
FIG. 23 shows an example of a screwdriver that can be used with the drill guide of FIG. 1.

Similarly, FIGS. 22 and 23 show a fixation pin and a screwdriver, respectively, sized and configured to be used in conjunction with drill guide assembly 10. Fixation pin 1200, shown in FIG. 22, similarly includes a handle 1210, main shaft 1220, and bone insertion end 1230. Fixation pin 1200 further comprises a stop 1240, for interaction with stop surface 692 (FIG. 13), such that fixation pin 1200 can be limited in its depth of insertion into a bone. Screwdriver 1300, shown in FIG. 23, similarly includes a handle 1310 and main shaft 1320. Main shaft 1320, like awl 1100 main shaft 1120 and fixation pin 1200 main shaft 1210 has an outer diameter slightly smaller than the inner diameter of guide barrel 40 such that the main shafts allow substantially only linear movement along and rotational movement about central axis CA. Screwdriver 1300 further comprises twist screw end 1330. Twist screw end 1330 can be sized and configured to engage a bone fixation screw (not shown) for insertion of the bone fixation screw into a patient's bone. According to one embodiment, screwdriver 1330 does not include a stop as provided on awl 1100 and fixation pin 1200 because the bone fixation screw comes to a stop against the bone plate hole configured to receive the head of the bone fixation screw.

While the invention has been shown and described herein with reference to particular embodiments, it is to be understood that the various additions, substitutions, or modifications of form, structure, arrangement, proportions, materials, and components and otherwise, used in the practice of the invention and which are particularly adapted to specific environments and operative requirements, may be made to the described embodiments without departing from the spirit and scope of the present invention. For example, the surgical drill guide assembly may have a single or duel guide sleeve. In a single format the guide sleeve is rotatable between a left and right position, thereby, allowing a left or right bone screw hole in a bone plate to be accessed. In addition, the handle member may include a grip that generally follows the contours of fingers that hold the grip. The presently disclosed embodiments are therefore to be considered in all respects as illustrative and not restrictive, the scope of the invention being indicated by the appended claims, and not limited to the foregoing description.

What is claimed:

1. A surgical drill guide, comprising:
a handle to be held by a user and configured to actuate a plate-engaging mechanism, the handle comprising first and second handle portions movably connected to each other;
an elongated member having proximal and distal portions, a length, and a longitudinal axis, the proximal portion associated with said first handle portion and the distal portion associated with a plate-engaging mechanism;
an actuating member having proximal and distal portions and a length, the proximal portion associated with the second handle portion and the distal portion associated with the plate-engaging mechanism; and
at least one guide sleeve having proximal and distal portions and a length, the proximal portions of the guide sleeve and said elongated member coupled to each other by a proximal coupling member having a length and the distal portions of said guide sleeve and the elongated member coupled together by a distal coupling member having a length, wherein the coupling member lengths are unequal;
wherein the length of the at least one guide sleeve is substantially the same as the length of the elongated member, and wherein the plate-engaging mechanism further comprises a bone plate-engaging portion configured to couple with a bone plate when the second handle portion is moved in a first direction with respect to said first handle portion.

2. The surgical drill guide of claim 1, wherein said first and second handle portions are pivotally connected.

3. The surgical drill guide of claim 1, wherein the handle further comprising a spring, the handle further having an actuated state and a non-actuated state, said spring associated with at least the first or second handle portion to bias the handle to the non-actuated state.

4. The surgical drill guide of claim 1, wherein the plate engaging mechanism further comprises a plate-engaging member and a locking assembly, wherein when the plate-engaging member contacts a recess in a bone plate, the locking assembly is operable to lock the plate-engaging mechanism to the plate without further operation by the user.

5. The surgical drill guide of claim 1, wherein the plate engaging mechanism further comprises a locking assembly including a sliding latch having a detent.

6. The surgical drill guide of claim 1, wherein the proximal portion of the elongated member is fixed to the first handle portion and the distal end of the elongated member is fixed to the plate engaging mechanism.

7. The surgical drill guide of claim 1, wherein the elongated member is fixed to the proximal and distal coupling members.

8. The surgical drill guide of claim 1, wherein the elongated member is integral with the first handle portion.

9. The surgical drill guide of claim 1, wherein the actuating member is integral with the second handle portion.

10. The surgical drill guide of claim 1, wherein the actuating member slidably engages the plate-engaging mechanism.

11. The surgical drill guide of claim 10, wherein the actuating member further comprises an actuating pin at the elongated member distal end for engaging the plate-engaging mechanism at a pin bore.

12. The surgical drill guide of claim 11, wherein the actuating pin is tapered at one end to correspond with a tapered bore in the plate-engaging mechanism.

13. The surgical drill guide of claim 1, wherein the plate-engaging mechanism further comprises a locator pin for engaging a slot in the bone plate, the locator pin operable to rotatably fix the drill guide to the bone plate.

14. The surgical drill guide of claim 13, wherein the locator pin is disposed substantially parallel with a longitudinal axis of the drill guide.

15. The surgical drill guide of claim 1, wherein the plate-engaging mechanism further comprises at least one resilient finger sized and configured to be radially expanded for engagement within a hole within the bone plate.

16. The surgical drill guide of claim 1, wherein when the drill guide engages the bone plate and the bone plate engages a spinal bone during an anterior approach surgical procedure on the spine, the guide sleeve is dimensioned and configured such that at least a portion of the proximal end of the guide sleeve is located outside of the patient's body.

17. The surgical drill guide of claim 1, wherein the length of the guide sleeve is from about 50 millimeters (mm) to about 400 mm.

18. The surgical drill guide of claim 1, wherein the length of the guide sleeve is about 250 mm to about 270 mm.

19. The surgical drill guide of claim 1, wherein the guide sleeve is sized to slidably accept at least one surgical tool for performing a surgical procedure.

20. The surgical drill guide of claim 1, wherein the guide sleeve inner diameter is from about 4 mm to about 15 mm.

21. The surgical drill guide of claim 1, wherein the guide sleeve inner diameter is about 8.0 mm to about 8.5 mm.

22. The surgical drill guide of claim 1, wherein said guide sleeve proximal portion further comprises a flange having a stop surface, the stop surface configured to contact a corresponding stop surface on a surgical tool when the tool is moved in a first direction within the guide tube, wherein when the corresponding stop surfaces contact each other the tool is prevented from further movement in the first direction.

23. The surgical drill guide of claim 1, wherein the guide sleeve has a longitudinal axis inclined from about 0 degrees to about 8 degrees with respect to the longitudinal axis of the elongated member.

24. The surgical drill guide of claim 1, wherein the guide sleeve has a longitudinal axis inclined about 2.0 to about 2.5 degrees with respect to the longitudinal axis of the elongated member.

25. The surgical drill guide of claim 1, further comprising at least first and second guide sleeves for accepting at least one tool for use in a surgical procedure.

26. The surgical drill guide of claim 1, wherein the first guide sleeve has a first longitudinal axis and the second guide sleeve has a second longitudinal axis, and wherein the first and second guide sleeves are disposed on opposite sides of the elongated member.

27. The surgical drill guide of claim 1, wherein the drill guide is configured for use as a plate holder.

28. The surgical drill guide of claim 1, wherein the plate-engaging mechanism engages a hole in the plate which aligns the at least one guide sleeve with a different hole in the plate.

29. A surgical drill guide, comprising:
a handle to be held by a user, and configured to actuate a plate-engaging mechanism, the handle comprising first and second handle portions movably connected to each other;
an elongated member having proximal and distal portions and a length, the proximal portion associated with the first handle portion;
an actuating member having proximal and distal portions and a length, the proximal portion associated with the second handle portion and the distal portion associated with a plate-engaging mechanism;
a guide sleeve having proximal and distal portions and a length, the proximal portions of said guide sleeve and said elongated member pivotably coupled to each other by a proximal pivot member, and the distal portions of said guide sleeve and elongated member pivotably coupled to each other by a distal pivot member; and the proximal and distal pivot members configured to rotatably couple said guide sleeve with said elongated member wherein said guide sleeve can rotate between at least a first position and a second position about a longitudinal axis of the elongated member;
wherein the plate-engaging mechanism further comprises a bone plate-engaging portion configured to couple with a bone plate when said second handle portion is moved with respect to said first handle portion.

30. The surgical drill guide of claim 29, wherein said first and second handle portions are pivotally connected.

31. The surgical drill guide of claim 30, wherein the first pivot member is coupled to the elongate member with a pin and the second pivot member is coupled with the plate-engaging mechanism with a pin.

32. The surgical drill guide of claim 31, wherein said pivot members are configured to align the guide sleeve with a left screw bore of the plate when in the first position and a right screw bore of the plate when in the second position.

33. The surgical drill guide of claim 31, wherein an angle between a central axis of the guide sleeve and a longitudinal axis of the elongated member is maintained whether the guide sleeve is in a first or second position.

34. The surgical drill guide of claim 29, wherein the handle further comprises a spring, the handle further having an actuated state and a non-actuated state, said spring associated with at least the first or second handle portion to bias the handle in the non-actuated state.

35. The surgical drill guide of claim 29, wherein the plate engaging mechanism further comprising a plate-engaging member and a locking assembly, wherein when the plate-engaging member contacts a correspondingly configured recess in a bone plate, the locking assembly is operable to lock the plate-engaging mechanism to the plate without further operation by the user.

36. The surgical drill guide of claim 29, wherein the plate engaging mechanism further comprises a locking assembly including a sliding latch having a detent.

37. The surgical drill guide of claim 29, wherein the proximal portion of the elongated member is fixed to the first handle portion and the distal end of the elongated member is fixed to the plate engaging mechanism.

38. The surgical drill guide of claim 29, wherein the elongated member is fixed to the proximal and distal pivot members.

39. The surgical drill guide of claim 29, wherein the actuating member slidably engages the plate-engaging mechanism.

40. The surgical drill guide of claim 39, wherein the actuating member further comprises an actuating pin at the member distal end for engaging the plate-engaging mechanism.

41. The surgical drill guide of claim 40, wherein the actuating pin is tapered at one end to correspond with a tapered bore in the plate-engaging mechanism.

42. The surgical drill guide of claim 29, wherein the plate-engaging mechanism further comprises a locator pin for engaging a hole in the bone plate, the locator pin operable to rotatably fix the drill guide to the bone plate.

43. The surgical drill guide of claim 42, wherein the locator pin is disposed substantially parallel with a longitudinal axis of the drill guide.

44. The surgical drill guide of claim 29, wherein the plate-engaging mechanism further comprises at least one resilient finger sized and configured to be radially expanded for engagement within a slot within the bone plate.

45. The surgical drill guide of claim 29, wherein when the drill guide engages the bone plate and the bone plate engages a spinal bone during an anterior approach surgical procedure on the spine, at least a portion of the guide sleeve is located outside of the patient's body.

46. The surgical drill guide of claim 29, wherein the length of the guide sleeve is from about 50 millimeters (mm) to about 400 mm.

47. The surgical drill guide of claim 29, wherein the length of the guide sleeve is about 250 mm to about 270 mm.

48. The surgical drill guide of claim 29, wherein the guide sleeve is sized to slidably accept at least one surgical tool for performing a surgical procedure.

49. The surgical drill guide of claim 29, wherein the guide sleeve inner diameter is from about 4 mm to about 15 mm.

50. The surgical drill guide of claim 29, wherein the guide sleeve inner diameter is about 8.0 mm to about 8.5 mm.

51. The surgical drill guide of claim 29, wherein said guide sleeve proximal portion further comprises a flange having a stop surface, the stop surface configured to contact a corresponding stop surface on a surgical tool when the tool is moved in a first direction within the guide tube, wherein when the corresponding surfaces contact each other the tool is prevented from further movement in the first direction.

52. The surgical drill guide of claim 29, wherein the guide sleeve has a longitudinal axis inclined from about 0 degrees to about 8 degrees with respect to a longitudinal axis of the elongated member.

53. The surgical drill guide of claim 29, wherein the guide sleeve has a longitudinal axis inclined about 2.0 to about 2.5 degrees with respect to the longitudinal axis of the elongated member.

54. The surgical drill guide of claim 29, wherein the drill guide is configured for use as a plate holder.

55. The surgical drill guide of claim 29, wherein said pivot members comprise elongated member-engaging portions for engaging the elongated member and guide sleeve-engaging portions for engaging the guide sleeve.

56. The surgical drill guide of claim 29, wherein the pivot members are configured to rotate about 180 degrees.

57. A guide assembly for guiding either an instrument or bone fastener at an appropriate angle with respect to a bone fixation device, the guide assembly comprising:
- a bone fixation device engaging mechanism having at least one radially extending member that engages at least one of a plurality of holes in a bone fixation device;
- a handle to be held by a user and configured to activate the engaging mechanism to attach the guide assembly to the bone fixation device, the handle having first and second handle portions moveable with respect to each other to attach and thereafter release the guide assembly from the bone fixation device;
- an elongated member having proximal and distal portions and a longitudinal axis, the proximal portion associated with the first handle portion and the distal portion associated with the engaging mechanism;
- an actuating member having proximal and distal portions, the proximal portion associated with the second handle position and the distal portion associated with the engaging mechanism;
- at least one guide sleeve having proximal and distal portions and a longitudinal axis, the guide sleeve sized to receive and guide either an instrument or bone fastener or both;
- a proximal coupling member coupling the proximal portion of the guide sleeve to the elongated member; and
- a distal coupling member coupling the distal portion of the guide sleeve to the elongated member,
- wherein the longitudinal axis of the elongated member is angled with respect to the longitudinal axis of the guide sleeve and the distal portion of the guide sleeve is aligned with a different hole than the hole engaged by the engaging mechanism.

58. The guide assembly of claim 57, wherein the guide sleeve is configured and adapted to protect soft tissue during the medical procedure.

* * * * *

UNITED STATES PATENT AND TRADEMARK OFFICE
CERTIFICATE OF CORRECTION

| | | |
|---|---|---|
| PATENT NO. | : 7,081,119 B2 | Page 1 of 1 |
| APPLICATION NO. | : 10/903649 | |
| DATED | : July 25, 2006 | |
| INVENTOR(S) | : Stihl | |

It is certified that error appears in the above-identified patent and that said Letters Patent is hereby corrected as shown below:

In claim 29, column 23, line 20:

Please replace the phrase "second handle portion" to -- first handle portion -- .

Signed and Sealed this

Twenty-seventh Day of March, 2007

JON W. DUDAS
*Director of the United States Patent and Trademark Office*